United States Patent
Stoecker et al.

(10) Patent No.: US 10,138,285 B2
(45) Date of Patent: Nov. 27, 2018

(54) DIAGNOSIS OF A NEUROAUTOIMMUNE DISEASE COMPRISING MEASURING AUTOANTIBODIES TO FLOTILLIN1 AND/OR FLOTILLIN2

(71) Applicant: EUROIMMUN MEDIZINISCHE LABORDIAGNOSTIKA AG, Luebeck (DE)

(72) Inventors: Winfried Stoecker, Gross Groenau (DE); Lars Komorowski, Ratzeburg (DE); Madeleine Scharf, Luebeck (DE); Ramona Miske, Luebeck (DE); Yvonne Denno, Luebeck (DE); Inga-Madeleine Dettmann, Ahrensboek (DE); Christian Probst, Ratzeburg (DE); Stefanie Hahn, Reinfeld (DE); Stephanie Kade, Wismar (DE); George Trendelenburg, Goettingen (DE)

(73) Assignee: EUROIMMUN MEDIZINISCHE LABORDIAGNOSTIKA AG, Luebeck (DE)

( * ) Notice: Subject to any disclaimer, the term of this patent is extended or adjusted under 35 U.S.C. 154(b) by 0 days.

(21) Appl. No.: 15/172,450

(22) Filed: Jun. 3, 2016

(65) Prior Publication Data

US 2016/0355565 A1 Dec. 8, 2016

(30) Foreign Application Priority Data

Jun. 4, 2015 (EP) .................................. 15001671
Jan. 28, 2016 (EP) .................................. 16000200

(51) Int. Cl.
| | |
|---|---|
| *C07K 14/705* | (2006.01) |
| *C07K 14/00* | (2006.01) |
| *C07K 14/47* | (2006.01) |
| *G01N 33/564* | (2006.01) |
| *G01N 33/68* | (2006.01) |
| *C07K 16/28* | (2006.01) |
| *A61K 38/00* | (2006.01) |

(52) U.S. Cl.
CPC ............ *C07K 14/705* (2013.01); *C07K 14/00* (2013.01); *C07K 14/4713* (2013.01); *C07K 16/28* (2013.01); *G01N 33/564* (2013.01); *G01N 33/6854* (2013.01); *G01N 33/6893* (2013.01); *G01N 33/6896* (2013.01); *A61K 38/00* (2013.01); *C07B 2200/11* (2013.01); *C07K 2317/20* (2013.01); *G01N 2333/47* (2013.01); *G01N 2800/16* (2013.01); *G01N 2800/28* (2013.01); *G01N 2800/285* (2013.01); *G01N 2800/7095* (2013.01)

(58) Field of Classification Search
None
See application file for complete search history.

(56) References Cited

U.S. PATENT DOCUMENTS

| | | |
|---|---|---|
| 2004/0053265 A1 | 3/2004 | Hipfel et al. |
| 2012/0114666 A1 | 5/2012 | Vincent |
| 2014/0141449 A1* | 5/2014 | Sarwal ................ G01N 33/564 435/7.1 |

FOREIGN PATENT DOCUMENTS

| | | |
|---|---|---|
| WO | WO 02/16636 A2 | 2/2002 |
| WO | WO 2010/046716 A1 | 4/2010 |
| WO | WO 2012/139051 A2 | 10/2012 |

OTHER PUBLICATIONS

Astorri et al., Horm Metab Res, 2010; 42: 955-960. (Year: 2010).*
Shervani et al., European Journal of Clinical Investigation, 2004; 34: 752-758. (Year: 2004).*
Hahn et al. Journal of Neuroinflammation, 2017; 14:123 (Year: 2017).*
Extended European Search Report dated Oct. 29, 2015 in Patent Application No. 15001671.5.
Extended European Search Report dated Apr. 12, 2016 in Patent Application No. 16000200.2.
Ksenia A. Arkhipova, et al., "Simultaneous expression of flotillin-1, flotillin-2, stomatin and caveolin-1 in non-small cell lung cancer and soft tissue sarcomas" BMC Cancer, 2014, vol. 14, No. 1, XP021177521, pp. 1-10.
Feng Zhao, et al., "Research advances on flotillins" Virology Journal, 2011, vol. 8, No. 1, XP021114037, pp. 1-9.
Claudia A. O. Stuermer, et al., "The 'lipid raft' microdomain proteins reggie-1 and reggie-2 (flotillins) are scaffolds for protein interaction and signaling" Biochemical Society Symposia, 2005, vol. 72, pp. 109-118.
W. Stöcker, et al., "Autoimmunity to Pancreatic Juice in Crohn's Disease: Results of an Autoantibody Screening in Patients with Chronic Inflammatory Bowel Disease" Concepts and Controversy in Gastroenterology, Scandinavian Journal of Gastroenterology, Sep. 1986, 16 pages.

* cited by examiner

*Primary Examiner* — Christina M Borgeest
(74) *Attorney, Agent, or Firm* — Grüneberg and Myers PLLC

(57) ABSTRACT

A method for diagnosing a disease by detecting an autoantibody that binds to flotillin1 and/or flotillin2 in a sample, a polypeptide comprising flotillin1 and/or flotillin2 or a variant thereof, which may be immobilized, a method of treating a disease by applying to a subject the polypeptide that binds to an autoantibody, an autoantibody binding to flotillin1 and/or flotillin2, a method for isolating the autoantibody, a pharmaceutical composition, a medical device and test kit comprising the polypeptide, are provided. A method for detecting the presence of an autoantibody is also provided.

3 Claims, 5 Drawing Sheets
(5 of 5 Drawing Sheet(s) Filed in Color)
Specification includes a Sequence Listing.

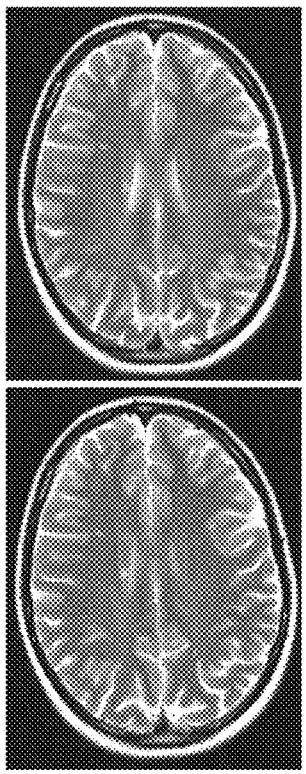
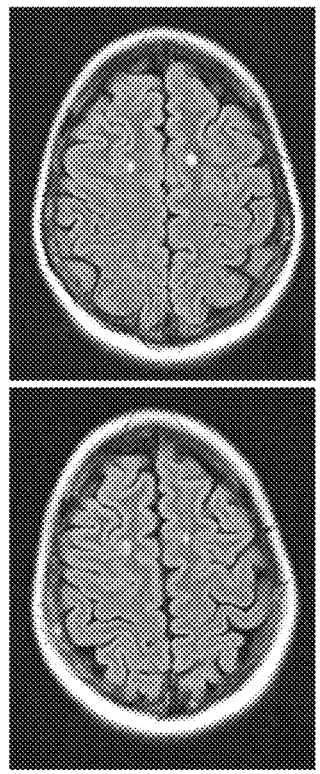
FIG. 1A  FIG. 1B  FIG. 1C  FIG. 1D
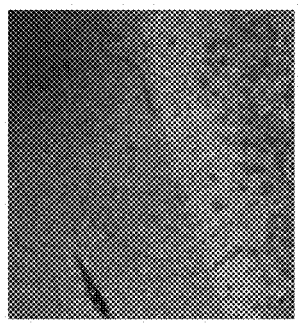
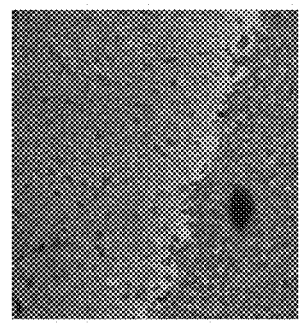
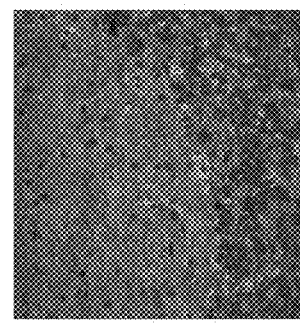
FIG. 2A  FIG. 2B  FIG. 2C

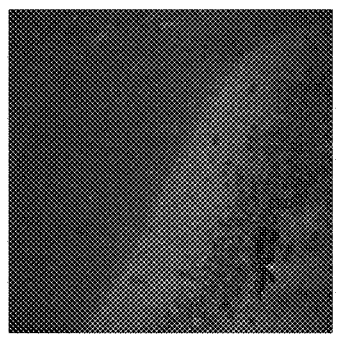 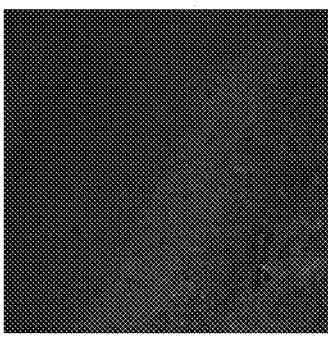 
FIG. 3B1  FIG. 3B2  FIG. 3B3
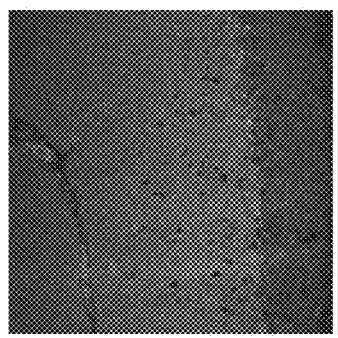 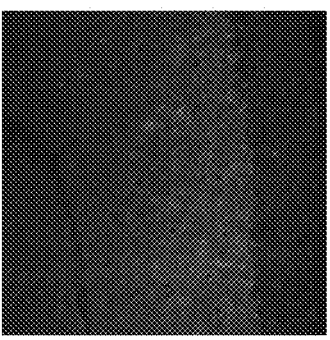 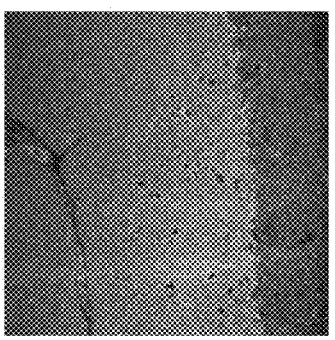
FIG. 3B4  FIG. 3B5  FIG. 3B6

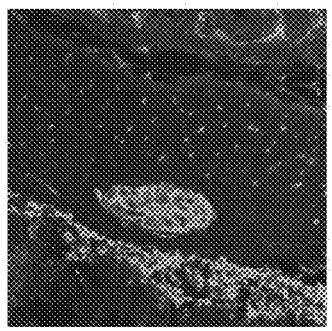
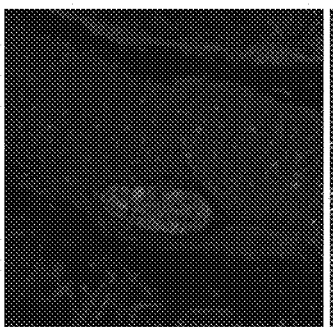
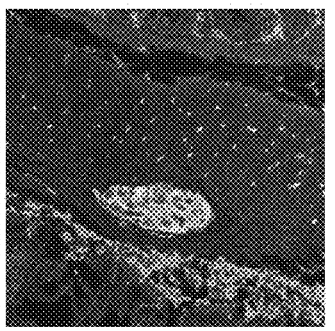
FIG. 3B7  FIG. 3B8  FIG. 3B9
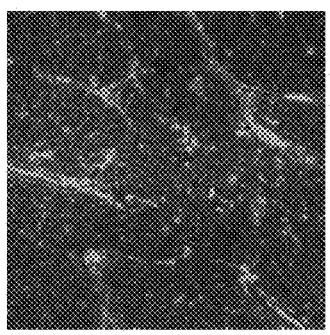
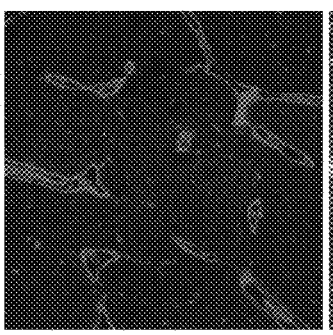
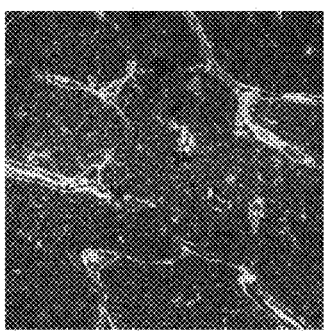
FIG. 3B10  FIG. 3B11  FIG. 3B12

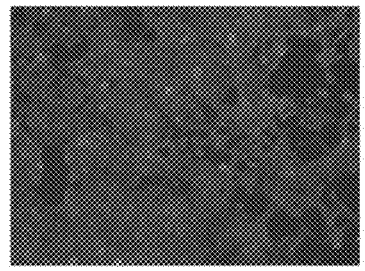
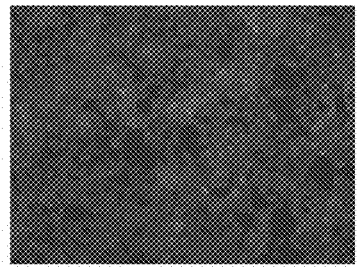
FIG. 4A1  FIG. 4A2
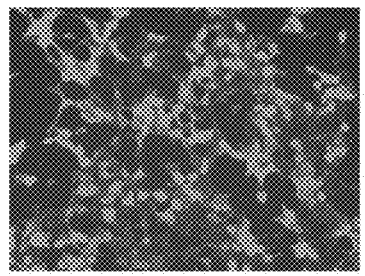
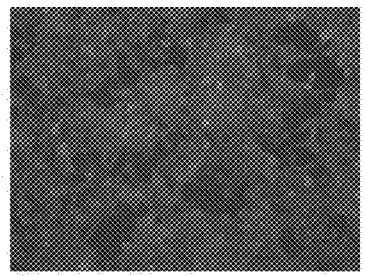
FIG. 4A3  FIG. 4A4
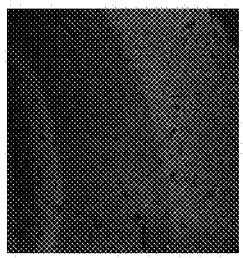
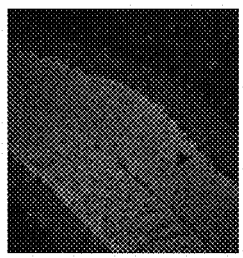
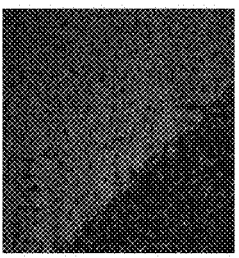
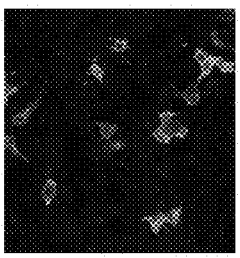
FIG. 4B1  FIG. 4B2  FIG. 4B3  FIG. 4B4
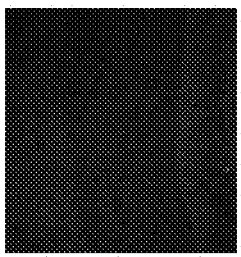
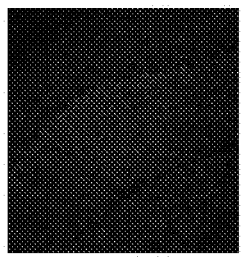
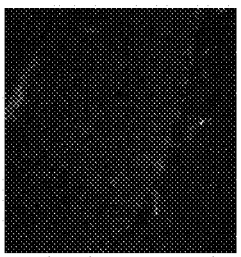
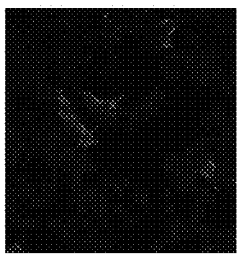
FIG. 4B5  FIG. 4B6  FIG. 4B7  FIG. 4B8

SEQUENCE LISTING

<160> NUMBER OF SEQ ID NOS: 8

<210> SEQ ID NO 1
<211> LENGTH: 6895
<212> TYPE: DNA
<213> ORGANISM: Artificial Sequence
<220> FEATURE:
<223> OTHER INFORMATION: pTriEx-1-Flotillin-1[human]-His

<400> SEQUENCE: 1

| | | | | | | |
|---|---|---|---|---|---|---|
| taatacgact | cactataggg | gaattgtgag | cggataacaa | ttcccggag | ttaatccggg | 60 |
| acctttaatt | caacccaaca | caatatatta | tagttaaata | agaattatta | tcaaatcatt | 120 |
| tgtatattaa | ttaaaatact | atactgtaaa | ttacatttta | tttacaatca | aaggagatat | 180 |
| accatgtttt | tcacttgtgg | cccaaatgag | gccatggtgg | tctccgggtt | ctgccgaagc | 240 |
| cccccagtca | tggtggctgg | agggcgtgtc | tttgtcctgc | cctgcatcca | acagatccag | 300 |
| aggatctctc | tcaacacact | gaccctcaat | gtcaagagtg | aaaaggttta | cactcgccat | 360 |
| ggggtcccca | tctcagtcac | tggcattgcc | caggtaaaaa | tccaggggca | gaacaaggag | 420 |
| atgttggcgg | ccgcctgtca | gatgttcctg | gggaagacgg | aggctgagat | tgcccacatt | 480 |
| gccctggaga | cgttagaggg | ccaccagagg | gccatcatgg | cccacatgac | tgtggaggag | 540 |
| atctataagg | acaggcagaa | attctcagaa | caggttttca | aagtggcctc | ctcagacctg | 600 |
| gtcaacatgg | gcatcagtgt | ggttagctac | actctgaagg | acattcacga | tgaccaggac | 660 |
| tatttgcact | ctttggggaa | ggctcgaaca | gctcaagtcc | aaaaagatgc | acggattgga | 720 |
| gaagcagagg | ccaagagaga | tgctgggatc | cgggaagcta | aagccaagca | ggaaaaggtg | 780 |
| tctgctcagt | acctgagtga | gatcgagatg | gccaaggcac | agagagatta | cgaactgaag | 840 |
| aaggccgcct | atgacatcga | ggtcaacacc | cgccgagcac | aggctgacct | ggcctatcag | 900 |
| cttcaggtgg | ccaagactaa | gcagcagatt | gaggagcagc | gggtgcaggt | gcaggtggtg | 960 |
| gagcgggccc | agcaggtggc | agtgcaggag | caggagatcg | cccggcggga | aaggagctg | 1020 |
| gaggcccggg | tgcggaagcc | agcggaagcg | gagcgctaca | agctgagcg | cctagccgag | 1080 |
| gcagagaagt | cccaactaat | tatgcaggcg | gaggcagaag | ccgcgtctgt | gcggatgcgt | 1140 |
| ggggaagctg | aggcctttgc | catagggggcc | cgagcccgag | ccgaggctga | gcagatggcc | 1200 |
| aagaaggcag | aagccttcca | gctgtaccaa | gaggctgctc | agctggacat | gctgctagag | 1260 |
| aagctgcccc | aggtggcaga | ggagatcagt | ggtcccttga | cttcagccaa | taagatcaca | 1320 |
| ctggtgtcca | gcggcagtgg | gaccatgggg | gcagccaaag | tgactgggga | agtactggac | 1380 |
| attctaactc | gcctgccaga | gagtgtggaa | agactcacag | gcgtgagcat | ctcccaggtg | 1440 |
| aatcacaagc | ctttgagaac | agccatcgag | caccaccatc | accatcacca | tcactaagtg | 1500 |
| attaacctca | ggtgcaggct | gcctatcaga | aggtggtggc | tggtgtggcc | aatgccctgg | 1560 |
| ctcacaaata | ccactgagat | cgatcttttt | ccctctgcca | aaaattatgg | ggacatcatg | 1620 |
| aagcccttg | agcatctgac | ttctggctaa | taaaggaaat | ttatttcat | tgcaatagtg | 1680 |
| tgttggaatt | ttttgtgtct | ctcactcgga | aggacatatg | ggagggcaaa | tcatttaaaa | 1740 |
| catcagaatg | agtatttggt | ttagagtttg | gcaacatatg | cccatatgta | actagcataa | 1800 |
| ccccttgggg | cctctaaacg | ggtcttgagg | ggttttttgc | tgaaagcatg | cggaggaaat | 1860 |
| tctccttgaa | gtttccctgg | tgttcaaagt | aaaggagttt | gcaccagacg | cacctctgtt | 1920 |
| cactggtccg | gcgtattaaa | acacgataca | ttgttattag | tacatttatt | aagcgctaga | 1980 |
| ttctgtgcgt | tgttgattta | cagacaattg | ttgtacgtat | tttaataatt | cattaaattt | 2040 |

```
ataatcttta gggtggtatg ttagagcgaa aatcaaatga ttttcagcgt ctttatatct    2100
gaatttaaat attaaatcct caatagattt gtaaaatagg tttcgattag tttcaaacaa    2160
gggttgtttt tccgaaccga tggctggact atctaatgga ttttcgctca acgccacaaa    2220
acttgccaaa tcttgtagca gcaatctagc tttgtcgata ttcgtttgtg ttttgttttg    2280
taataaaggt tcgacgtcgt tcaaaatatt atgcgctttt gtatttcttt catcactgtc    2340
gttagtgtac aattgactcg acgtaaacac gttaaataga gcttggacat atttaacatc    2400
gggcgtgtta gctttattag gccgattatc gtcgtcgtcc caaccctcgt cgttagaagt    2460
tgcttccgaa gacgattttg ccatagccac acgacgccta ttaattgtgt cggctaacac    2520
gtccgcgatc aaatttgtag ttgagctttt tggaattatt tctgattgcg ggcgttttg     2580 ggcgggtttc aatctaactg tgcccgattt taattcagac aacacgttag aaagcgatgg    2640
tgcaggcggt ggtaacattt cagacggcaa atctactaat ggcggcggtg gtggagctga    2700
tgataaatct accatcggtg gaggcgcagg cggggctggc ggcggaggcg gaggcggagg    2760
tggtggcggt gatgcagacg gcggtttagg ctcaaatgtc tctttaggca acacagtcgg    2820
cacctcaact attgtactgg tttcgggcgc cgttttggt ttgaccggtc tgagacgagt     2880
gcgatttttt tcgtttctaa tagcttccaa caattgttgt ctgtcgtcta aggtgcagc    2940 gggttgaggt tccgtcggca ttggtggagc gggcggcaat tcagacatcg atggtggtgg    3000
tggtggtgga ggcgctggaa tgttaggcac gggagaaggt ggtggcggcg gtgccgccgg    3060
tataatttgt tctggtttag tttgttcgcg cacgattgtg ggcaccggcg caggcgccgc    3120
tggctgcaca acggaaggtc gtctgcttcg aggcagcgct tggggtggtg gcaattcaat    3180
attataattg gaatacaaat cgtaaaaatc tgctataagc attgtaattt cgctatcgtt    3240
taccgtgccg atatttaaca accgctcaat gtaagcaatt gtattgtaaa gagattgtct    3300
caagctcgga acgctgcgct cggtcgttcg gctgcggcga gcggtatcag ctcactcaaa    3360
ggcggtaata cggttatcca cagaatcagg ggataacgca ggaaagaaca tgtgagcaaa    3420
aggccagcaa aaggccagga accgtaaaaa ggccgcgttg ctggcgtttt tccataggct    3480
ccgcccccct gacgagcatc acaaaaatcg acgctcaagt cagaggtggc gaaacccgac    3540
aggactataa agataccagg cgtttccccc tggaagctcc ctcgtgcgct ctcctgttcc    3600
gaccctgccg cttaccggat acctgtccgc ctttctccct tcgggaagcg tggcgctttc    3660
tcaatgctca cgctgtaggt atctcagttc ggtgtaggtc gttcgctcca agctgggctg    3720
tgtgcacgaa ccccccgttc agcccgaccg ctgcgcctta tccggtaact atcgtcttga    3780
gtccaacccg gtaagacacg acttatcgcc actggcagca gccactggta acaggattag    3840
cagagcgagg tatgtaggcg gtgctacaga gttcttgaag tggtggccta actacggcta    3900
cactagaagg acagtatttg gtatctgcgc tctgctgaag ccagttacct tcggaaaaag    3960
agttggtagc tcttgatccg gcaaacaaac caccgctggt agcggtggtt ttttgtttg    4020 caagcagcag attacgcgca gaaaaaaagg atctcaagaa gatcctttgt taccaatgct    4080
taatcagtga ggcacctatc tcagcgatct gtctatttcg ttcatccata gttgcctgac    4140
tccccgtcgt gtagataact acgatacggg agggcttacc atctggcccc agtgctgcaa    4200
tgataccgcg agacccacgc tcaccggctc cagatttatc agcaataaac cagccagccg    4260
gaagggccga gcgcagaagt ggtcctgcaa ctttatccgc ctccatccag tctattaatt    4320
gttgccggga agctagagta agtagttcgc cagttaatag tttgcgcaac gttgttgcca    4380
```

```
ttgctacagg catcgtggtg tcacgctcgt cgtttggtat ggcttcattc agctccggtt    4440
cccaacgatc aaggcgagtt acatgatccc ccatgttgtg caaaaaagcg gttagctcct    4500
tcggtcctcc gatcgttgtc agaagtaagt tggccgcagt gttatcactc atggttatgg    4560
cagcactgca taattctctt actgtcatgc catccgtaag atgcttttct gtgactggtg    4620
agtactcaac caagtcattc tgagaatagt gtatgcggcg accgagttgc tcttgcccgg    4680
cgtcaatacg ggataatacc cgcgccacata gcagaacttt aaaagtgctc atcattggaa    4740
aacgttcttc ggggcgaaaa ctctcaagga tcttaccgct gttgagatcc agttcgatgt    4800
aacccactcg tgcacccaac tgatcttcag catcttttac tttcaccagc gtttctgggt    4860
gagcaaaaac aggaaggcaa aatgccgcaa aaaagggaat aagggcgaca cggaaatgtt    4920
gaatactcat actcttcctt tttcaatatt attgaagcat ttatcagggt tattgtctca    4980
tgtccgcgcg tttcctgcat cttttaatca aatcccaaga tgtgtataaa ccaccaaact    5040
gccaaaaaat gaaaactgtc gacaagctct gtccgtttgc tggcaactgc aagggtctca    5100
atcctatttg taattattga ataataaaac aattataaat gtcaaatttg ttttttatta    5160
acgatacaaa ccaaacgcaa caagaacatt tgtagtatta tctataattg aaaacgcgta    5220
gttataatcg ctgaggtaat atttaaaatc attttcaaat gattcacagt taatttgcga    5280
caatataatt ttattttcac ataaactaga cgccttgtcg tcttcttctt cgtattcctt    5340
ctcttttca tttttctctt cataaaaatt aacatagtta ttatcgtatc catatatgta    5400
tctatcgtat agagtaaatt ttttgttgtc ataaatatat atgtcttttt taatggggtg    5460
tatagtaccg ctgcgcatag ttttttctgta atttacaaca gtgctatttt ctggtagttc    5520
ttcggagtgt gttgctttaa ttattaaatt tatataatca atgaatttgg gatcgtcggt    5580
tttgtacaat atgttgccgg catagtacgc agcttcttct agttcaatta caccattttt    5640
tagcagcacc ggattaacat aacttttccaa aatgttgtac gaaccgttaa acaaaaacag    5700
ttcacctccc ttttctatac tattgtctgc gagcagttgt ttgttgttaa aaataacagc    5760
cattgtaatg agacgcacaa actaatatca caaactggaa atgtctatca atatatagtt    5820
gctctagtta ttaatagtaa tcaattacgg ggtcattagt tcatagccca tatatggagt    5880
tccgcgttac ataacttacg gtaaatggcc cgcctggctg accgcccaac gacccccgcc    5940
cattgacgtc aataatgacg tatgttccca tagtaacgcc aatagggact ttccattgac    6000
gtcaatgggt ggactattta cggtaaactg cccacttggc agtacatcaa gtgtatcata    6060
tgccaagtac gccccctatt gacgtcaatg acggtaaatg gcccgcctgg cattatgccc    6120
agtacatgac cttatgggac tttcctactt ggcagtacat ctacgtatta gtcatcgcta    6180
ttaccatgca tggtcgaggt gagccccacg ttctgcttca ctctccccat ctccccccc    6240
tccccacccc caattttgta tttatttatt ttttaattat tttgtgcagc gatggggggcg    6300
gggggggggg gggggcgcgc gccaggcggg gcggggcggg gcgaggggcg gggcggggcg    6360
aggcggagag gtgcggcggc agccaatcag agcggcgcgc tccgaaagtt tccttttatg    6420
gcgaggcggc ggcggcggcg gccctataaa aagcgaagcg cgcggcgggc gggagtcgct    6480
gcgacgctgc cttcgccccg tgccccgctc cgcgccgcc tcgcgccgcc cgccccggct    6540
ctgactgacc gcgttactcc cacaggtgag cgggcgggac ggcccttctc cttcgggctg    6600
taattagcgc ttggtttaat gacggcttgt ttcttttctg tggctgcgtg aaagccttga    6660
ggggctccgg gagggccctt tgtgcggggg gagcggctcg ggctgtccg cggggggacg    6720
gctgccttcg gggggacgg ggcagggcgg ggttcggctt ctggcgtgtg accggcggct    6780
```

```
ctagagcctc tgctaaccat gttcatgcct tcttcttttt cctacagctc ctgggcaacg    6840
tgctggttat tgtgctgtct catcattttg gcaaagaatt ggatcggacc gaaat         6895
```

<210> SEQ ID NO 2
<211> LENGTH: 437
<212> TYPE: PRT
<213> ORGANISM: Artificial Sequence
<220> FEATURE:
<223> OTHER INFORMATION: Flotillin-1[human]-His

<400> SEQUENCE: 2

```
Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
            20                  25                  30

Pro Cys Ile Gln Gln Ile Gln Arg Ile Ser Leu Asn Thr Leu Thr Leu
        35                  40                  45

Asn Val Lys Ser Glu Lys Val Tyr Thr Arg His Gly Val Pro Ile Ser
    50                  55                  60

Val Thr Gly Ile Ala Gln Val Lys Ile Gln Gly Gln Asn Lys Glu Met
65                  70                  75                  80

Leu Ala Ala Ala Cys Gln Met Phe Leu Gly Lys Thr Glu Ala Glu Ile
                85                  90                  95

Ala His Ile Ala Leu Glu Thr Leu Glu Gly His Gln Arg Ala Ile Met
            100                 105                 110

Ala His Met Thr Val Glu Glu Ile Tyr Lys Asp Arg Gln Lys Phe Ser
        115                 120                 125

Glu Gln Val Phe Lys Val Ala Ser Ser Asp Leu Val Asn Met Gly Ile
    130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
            180                 185                 190

Lys Ala Lys Gln Glu Lys Val Ser Ala Gln Tyr Leu Ser Glu Ile Glu
        195                 200                 205

Met Ala Lys Ala Gln Arg Asp Tyr Glu Leu Lys Lys Ala Ala Tyr Asp
    210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Gln Arg Val Gln Val
                245                 250                 255

Gln Val Val Glu Arg Ala Gln Gln Val Ala Val Gln Glu Gln Glu Ile
            260                 265                 270

Ala Arg Arg Glu Lys Glu Leu Glu Ala Arg Val Arg Lys Pro Ala Glu
        275                 280                 285

Ala Glu Arg Tyr Lys Leu Glu Arg Leu Ala Glu Ala Glu Lys Ser Gln
    290                 295                 300

Leu Ile Met Gln Ala Glu Ala Glu Ala Ala Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Leu Tyr Gln Glu Ala Ala
```

```
                340             345             350
Gln Leu Asp Met Leu Leu Glu Lys Leu Pro Gln Val Ala Glu Glu Ile
        355                 360                 365

Ser Gly Pro Leu Thr Ser Ala Asn Lys Ile Thr Leu Val Ser Ser Gly
        370                 375                 380

Ser Gly Thr Met Gly Ala Ala Lys Val Thr Gly Glu Val Leu Asp Ile
385                 390                 395                 400

Leu Thr Arg Leu Pro Glu Ser Val Glu Arg Leu Thr Gly Val Ser Ile
                405                 410                 415

Ser Gln Val Asn His Lys Pro Leu Arg Thr Ala Ile Glu His His His
                420                 425                 430

His His His His His
        435

<210> SEQ ID NO 3
<211> LENGTH: 6897
<212> TYPE: DNA
<213> ORGANISM: Artificial Sequence
<220> FEATURE:
<223> OTHER INFORMATION: pTriEx-1-Flotillin-1[human]

<400> SEQUENCE: 3
taatacgact cactataggg gaattgtgag cggataacaa ttcccccggag ttaatccggg    60 acctttaatt caacccaaca caatatatta tagttaaata agaattatta tcaaatcatt   120
tgtatattaa ttaaaatact atactgtaaa ttcattttta tttacaatca aaggagatat   180
accatgtttt tcacttgtgg cccaaatgag gccatggtgg tctccgggtt ctgccgaagc   240
cccccagtca tggtggctgg agggcgtgtc tttgtcctgc cctgcatcca acagatccag   300
aggatctctc tcaacacact gaccctcaat gtcaagagtg aaaaggttta cactcgccat   360
ggggtcccca tctcagtcac tggcattgcc caggtaaaaa tccagggca gaacaaggag   420 atgttggcgg ccgcctgtca gatgttcctg gggaagacgg aggctgagat tgcccacatt   480
gccctggaga cgttagaggg ccaccagagg gccatcatgg cccacatgac tgtggaggag   540
atctataagg acaggcagaa attctcagaa caggttttca agtggcctc ctcagacctg   600 gtcaacatgg gcatcagtgt ggttagctac actctgaagg acattcacga tgaccaggac   660
tatttgcact ctttggggaa ggctcgaaca gctcaagtcc aaaaagatgc acggattgga   720
gaagcagagg ccaagagaga tgctgggatc cgggaagcta agccaagca ggaaaaggtg   780 tctgctcagt acctgagtga gatcgagatg gccaaggcac agagagatta cgaactgaag   840
aaggccgcct atgacatcga ggtcaacacc cgccgagcac aggctgacct ggcctatcag   900
cttcaggtgg ccaagactaa gcagcagatt gaggagcagc gggtgcaggt gcaggtggtg   960
gagcgggccc agcaggtggc agtgcaggag caggagatcg cccggcggga aaggagctg  1020 gaggcccggg tgcggaagcc agcggaagcg gagcgctaca agctggagcg cctagccgag  1080
gcagagaagt cccaactaat tatgcaggcg gaggcagaag ccgcgtctgt gcggatgcgt  1140
ggggaagctg aggcctttgc catagggcc cgagcccgag ccgaggctga gcagatggcc  1200
aagaaggcag aagccttcca gctgtaccaa gaggctgctc agctggacat gctgctagag  1260
aagctgcccc aggtggcaga ggagatcagt ggtccctga cttcagccaa taagatcaca  1320
ctggtgtcca gcggcagtgg gaccatgggg gcagccaaag tgactgggga agtactggac  1380
attctaactc gcctgccaga gagtgtggaa agactcacag gcgtgagcat ctcccaggtg  1440
aatcacaagc ctttgagaac agcctgatcg agcaccacca tcaccatcac catcactaag  1500
```

```
tgattaacct caggtgcagg ctgcctatca gaaggtggtg gctggtgtgg ccaatgccct    1560
ggctcacaaa taccactgag atcgatcttt ttccctctgc caaaaattat ggggacatca    1620
tgaagcccct tgagcatctg acttctggct aataaaggaa atttattttc attgcaatag    1680
tgtgttggaa ttttttgtgt ctctcactcg aaggacata tggagggca aatcatttaa      1740 aacatcagaa tgagtatttg gtttagagtt tggcaacata tgcccatatg taactagcat    1800
aaccccttgg ggcctctaaa cgggtcttga ggggttttt gctgaaagca tgcggaggaa     1860
attctccttg aagtttccct ggtgttcaaa gtaaggagt ttgcaccaga cgcacctctg     1920
ttcactggtc cggcgtatta aaacacgata cattgttatt agtacattta ttaagcgcta    1980
gattctgtgc gttgttgatt tacagacaat tgttgtacgt attttaataa ttcattaaat    2040
ttataatctt tagggtggta tgttagagcg aaaatcaaat gattttcagc gtctttatat    2100
ctgaatttaa atattaaatc ctcaatagat ttgtaaaata ggtttcgatt agtttcaaac    2160
aagggttgtt tttccgaacc gatggctgga ctatctaatg gattttcgct caacgccaca    2220
aaacttgcca aatcttgtag cagcaatcta gctttgtcga tattcgtttg tgttttgttt    2280
tgtaataaag gttcgacgtc gttcaaaata ttatgcgctt ttgtatttct ttcatcactg    2340
tcgttagtgt acaattgact cgacgtaaac acgttaaata gagcttggac atatttaaca    2400
tcgggcgtgt tagcttat aggccgatta tcgtcgtcgt cccaacccctc gtcgttagaa     2460 gttgcttccg aagacgattt tgccatagcc acacgacgcc tattaattgt gtcggctaac    2520
acgtccgcga tcaaatttgt agttgagctt tttggaatta tttctgattg cgggcgtttt    2580
tgggcgggtt tcaatctaac tgtgcccgat tttaattcag acaacacgtt agaaagcgat    2640
ggtgcaggcg gtggtaacat ttcagacggc aaatctacta atggcggcgg tggtggagct    2700
gatgataaat ctaccatcgg tggaggcgca ggcggggctg gcggcggagg cggaggcgga    2760
ggtggtggcg gtgatgcaga cggcggttta ggctcaaatg tctctttagg caacacagtc    2820
ggcacctcaa ctattgtact ggtttcgggc gccgttttg gtttgaccgg tctgagacga     2880
gtgcgatttt tttcgtttct aatagcttcc aacaattgtt gtctgtcgtc taaaggtgca    2940
gcgggttgag gttccgtcgg cattggtgga gcggcggca attcagacat cgatggtggt    3000
ggtggtggtg gaggcgctgg aatgttaggc acgggagaag gtggtggcgg cggtgccgcc    3060
ggtataattt gttctggttt agtttgttcg cgcacgattg tgggcaccgg cgcaggcgcc    3120
gctggctgca acggaagg tcgtctgctt cgaggcagcg cttggggtgg tggcaattca     3180
atattataat tggaatacaa atcgtaaaaa tctgctataa gcattgtaat ttcgctatcg    3240
tttaccgtgc cgatatttaa caaccgctca atgtaagcaa ttgtattgta aagagattgt    3300
ctcaagctcg gaacgctgcg ctcggtcgtt cggctgcggc gagcggtatc agctcactca    3360
aaggcggtaa tacggttatc cacagaatca ggggataacg caggaaagaa catgtgagca    3420
aaaggccagc aaaaggccag gaaccgtaaa aaggccgcgt tgctggcgtt tttccatagg    3480
ctccgccccc ctgacgagca tcacaaaaat cgacgctcaa gtcagaggtg gcgaaacccg    3540
acaggactat aaagatacca ggcgtttccc cctggaagct ccctcgtgcg ctctcctgtt    3600
ccgaccctgc cgcttaccgg atacctgtcc gcctttctcc cttcgggaag cgtggcgctt    3660
tctcaatgct cacgctgtag gtatctcagt tcggtgtagg tcgttcgctc caagctgggc    3720
tgtgtgcacg aaccccccgt tcagcccgac cgctgcgcct tatccggtaa ctatcgtctt    3780
gagtccaacc cggtaagaca cgacttatcg ccactggcag cagccactgg taacaggatt    3840
```

-continued

```
agcagagcga ggtatgtagg cggtgctaca gagttcttga agtggtggcc taactacggc      3900
tacactagaa ggacagtatt tggtatctgc gctctgctga agccagttac cttcggaaaa      3960
agagttggta gctcttgatc cggcaaacaa accaccgctg gtagcggtgg ttttttttgtt     4020 tgcaagcagc agattacgcg cagaaaaaaa ggatctcaag aagatccttt gttaccaatg      4080
cttaatcagt gaggcaccta tctcagcgat ctgtctattt cgttcatcca tagttgcctg      4140
actccccgtc gtgtagataa ctacgatacg ggagggctta ccatctggcc ccagtgctgc      4200
aatgataccg cgagacccac gctcaccggc tccagattta tcagcaataa accagccagc     4260
cggaagggcc gagcgcagaa gtggtcctgc aactttatcc gcctccatcc agtctattaa      4320
ttgttgccgg gaagctagag taagtagttc gccagttaat agtttgcgca acgttgttgc      4380
cattgctaca ggcatcgtgg tgtcacgctc gtcgtttggt atggcttcat tcagctccgg      4440
ttcccaacga tcaaggcgag ttacatgatc ccccatgttg tgcaaaaaag cggttagctc      4500
cttcggtcct ccgatcgttg tcagaagtaa gttggccgca gtgttatcac tcatggttat      4560
ggcagcactg cataattctc ttactgtcat gccatccgta agatgctttt ctgtgactgg      4620
tgagtactca accaagtcat tctgagaata gtgtatgcgg cgaccgagtt gctcttgccc      4680
ggcgtcaata cgggataata ccgcgccaca tagcagaact ttaaaagtgc tcatcattgg      4740
aaaacgttct cggggcgaaa actctcaag gatcttaccg ctgttgagat ccagttcgat       4800
gtaacccact cgtgcaccca actgatcttc agcatctttt actttcacca gcgtttctgg      4860
gtgagcaaaa acaggaaggc aaaatgccgc aaaaaaggga ataagggcga cacggaaatg      4920
ttgaatactc atactcttcc tttttcaata ttattgaagc atttatcagg gttattgtct      4980
catgtccgcg cgtttcctgc atcttttaat caaatcccaa gatgtgtata aaccaccaaa      5040
ctgccaaaaa atgaaaactg tcgacaagct ctgtccgttt gctggcaact gcaagggtct      5100
caatcctatt tgtaattatt gaataataaa acaattataa atgtcaaatt tgtttttttat     5160 taacgataca aaccaaacgc aacaagaaca tttgtagtat tatctataat tgaaaacgcg      5220
tagttataat cgctgaggta atatttaaaa tcattttcaa atgattcaca gttaatttgc      5280
gacaatataa ttttatttc acataaacta gacgccttgt cgtcttcttc ttcgtattcc       5340 ttctctttt cattttctc ttcataaaaa ttaacatagt tattatcgta tccatatatg        5400
tatctatcgt atagagtaaa ttttttgttg tcataaatat atatgtcttt tttaatgggg      5460
tgtatagtac cgctgcgcat agtttttctg taatttacaa cagtgctatt ttctggtagt      5520
tcttcggagt gtgttgcttt aattattaaa tttatataat caatgaattt gggatcgtcg      5580
gttttgtaca atatgttgcc ggcatagtac gcagcttctt ctagttcaat tacaccatt      5640 tttagcagca ccggattaac ataactttcc aaaatgttgt acgaaccgtt aaacaaaaac      5700
agttcacctc cctttctat actattgtct gcgagcagtt gtttgttgtt aaaaataaca      5760
gccattgtaa tgagacgcac aaactaatat cacaaactgg aaatgtctat caatatatag      5820
ttgctctagt tattaatagt aatcaattac ggggtcatta gttcatagcc catatatgga      5880
gttccgcgtt acataactta cggtaaatgg cccgcctggc tgaccgccca acgacccccg      5940
cccattgacg tcaataatga cgtatgttcc catagtaacg ccaatagga ctttccattg       6000 acgtcaatgg gtggactatt tacggtaaac tgcccacttg gcagtacatc aagtgtatca      6060
tatgccaagt acgcccccta ttgacgtcaa tgacggtaaa tggcccgcct ggcattatgc      6120
ccagtacatg accttatggg actttcctac ttggcagtac atctacgtat tagtcatcgc      6180
tattaccatg catggtcgag gtgagcccca cgttctgctt cactctcccc atctcccccc      6240
```

```
cctcccccacc cccaattttg tatttattta ttttttaatt attttgtgca gcgatggggg    6300
cggggggggg ggggggggcgc gcgccaggcg gggcggggcg gggcgagggg cggggcgggg    6360
cgaggcggag aggtgcggcg gcagccaatc agagcggcgc gctccgaaag tttcctttta    6420
tggcgaggcg gcgcggcgg cggccctata aaaagcgaag cgcgcggcgg gcgggagtcg     6480
ctgcgacgct gccttcgccc cgtgccccgc tccgccgccg cctcgcgccc ccgccccgg     6540 ctctgactga ccgcgttact cccacaggtg agcgggcggg acggcccttc tccttcgggc    6600
tgtaattagc gcttggttta atgacggctt gtttcttttc tgtggctgcg tgaaagcctt    6660
gaggggctcc gggagggccc tttgtgcggg gggagcggct cggggctgtc cgcgggggga    6720
cggctgcctt cggggggggac ggggcagggc ggggttcggc ttctggcgtg tgaccggcgg   6780
ctctagagcc tctgctaacc atgttcatgc cttcttcttt ttcctacagc tcctgggcaa    6840
cgtgctggtt attgtgctgt ctcatcattt tggcaaagaa ttggatcgga ccgaaat       6897
```

<210> SEQ ID NO 4
<211> LENGTH: 427
<212> TYPE: PRT
<213> ORGANISM: Homo sapiens

<400> SEQUENCE: 4

```
Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
            20                  25                  30

Pro Cys Ile Gln Gln Ile Gln Arg Ile Ser Leu Asn Thr Leu Thr Leu
        35                  40                  45

Asn Val Lys Ser Glu Lys Val Tyr Thr Arg His Gly Val Pro Ile Ser
    50                  55                  60

Val Thr Gly Ile Ala Gln Val Lys Ile Gln Gly Gln Asn Lys Glu Met
65                  70                  75                  80

Leu Ala Ala Ala Cys Gln Met Phe Leu Gly Lys Thr Glu Ala Glu Ile
                85                  90                  95

Ala His Ile Ala Leu Glu Thr Leu Glu Gly His Gln Arg Ala Ile Met
            100                 105                 110

Ala His Met Thr Val Glu Glu Ile Tyr Lys Asp Arg Gln Lys Phe Ser
        115                 120                 125

Glu Gln Val Phe Lys Val Ala Ser Ser Asp Leu Val Asn Met Gly Ile
    130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
            180                 185                 190

Lys Ala Lys Gln Glu Lys Val Ser Ala Gln Tyr Leu Ser Glu Ile Glu
        195                 200                 205

Met Ala Lys Ala Gln Arg Asp Tyr Glu Leu Lys Ala Ala Tyr Asp
    210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Gln Arg Val Gln Val
                245                 250                 255
```

```
Gln Val Val Glu Arg Ala Gln Gln Val Ala Val Gln Glu Gln Glu Ile
            260                 265                 270

Ala Arg Arg Glu Lys Glu Leu Glu Ala Arg Val Arg Lys Pro Ala Glu
        275                 280                 285

Ala Glu Arg Tyr Lys Leu Glu Arg Leu Ala Glu Ala Glu Lys Ser Gln
        290                 295                 300

Leu Ile Met Gln Ala Glu Ala Glu Ala Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Leu Tyr Gln Glu Ala Ala
            340                 345                 350

Gln Leu Asp Met Leu Leu Glu Lys Leu Pro Gln Val Ala Glu Glu Ile
            355                 360                 365

Ser Gly Pro Leu Thr Ser Ala Asn Lys Ile Thr Leu Val Ser Ser Gly
        370                 375                 380

Ser Gly Thr Met Gly Ala Ala Lys Val Thr Gly Glu Val Leu Asp Ile
385                 390                 395                 400

Leu Thr Arg Leu Pro Glu Ser Val Glu Arg Leu Thr Gly Val Ser Ile
                405                 410                 415

Ser Gln Val Asn His Lys Pro Leu Arg Thr Ala
            420                 425

<210> SEQ ID NO 5
<211> LENGTH: 6898
<212> TYPE: DNA
<213> ORGANISM: Artificial Sequence
<220> FEATURE:
<223> OTHER INFORMATION: pTriEx-1-Flotillin-2[human]-His

<400> SEQUENCE: 5
taatacgact cactataggg gaattgtgag cggataacaa ttccccggag ttaatccggg      60
acctttaatt caacccaaca caatatatta tagttaaata agaattatta tcaaatcatt     120
tgtatattaa ttaaaatact atactgtaaa ttacatttta tttacaatca aaggagatat     180
accatgggca attgccacac ggtgggcccc aacgaggcac tggtggtctc aggggggctgt    240 tgtggttctg actacaagca gtatgtgttt ggcggctggg cttgggcctg gtggtgtatc     300
tcggacactc agaggatttc cctagagatt atgacgttgc agccccgctg tgaggacgta     360
gagacggccg aggggtagc tttaactgtg acgggtgtcg cccaggtgaa gatcatgacg      420
gagaaggagc tcctggctgt agcctgtgaa cagttcctgg gcaagaacgt gcaggacatt     480
aagaacgtcg tactgcagac cctggagggg catctacgct ccatccttgg gactctgact     540
gtggagcaga tttatcagga ccgagaccag tttgccaagc tggtgcggga agtggcagcc     600
cctgatgttg gccgtatggg catcgagatc ctcagcttca ccatcaagga tgtctatgac     660
aaagtagact atctgagctc cctgggcaag acacagactg ccgtggtaca gagagatgca     720
gacatcggtg tggcagaggc agagcgggac gcaggcatcc gggaagccga gtgcaagaag     780
gaaatgctag atgtgaagtt catggcagac accaagattg ctgactccaa gagagccttt     840
gagctgcaaa agtcagcctt cagtgaggag gtcaacatca gacagctga ggcccagttg      900 gcctatgagc tacaaggggc cagagagcaa cagaagatcc ggcaggaaga gattgagatt     960
gaggtagtac agcgcaagaa gcagatcgcc gtggaggcgc aggagatcct gcgcacagac    1020
aaggagctca tcgccacagt gcgccgccct gcagaggcag aggcccaccg catccagcag    1080
```

```
attgctgaag gcgaaaaggt gaaacaagtc ctcttggcac aagcagaagc tgagaagatt    1140
cgcaaaatcg gggaggcaga ggcagcagtc attgaggcca tgggcaaggc cgaggccgag    1200
cggatgaagc ttaaagctga ggcctaccag aagtacgggg atgcggccaa gatggccctg    1260
gtgctggagg ccctgcccca gattgctgcc aagatcgccg cacccctgac taaagtcgat    1320
gagattgtgg ttctcagtgg ggacaacagc aaggtgacat cagaagtgaa ccggctgcta    1380
gcagaactgc ctgcttctgt tcatgccctc actggtgtgg acctctcaaa gataccactg    1440
atcaagaaag ccactggtgt gcaggtgatc gagcaccacc atcaccatca ccatcactaa    1500
gtgattaacc tcaggtgcag gctgcctatc agaaggtggt ggctggtgtg gccaatgccc    1560
tggctcacaa ataccactga gatcgatctt tttccctctg ccaaaaatta tggggacatc    1620
atgaagcccc ttgagcatct gacttctggc taataaagga aatttatttt cattgcaata    1680
gtgtgttgga attttttgtg tctctcactc ggaaggacat atgggagggc aaatcattta    1740
aaacatcaga atgagtattt ggtttagagt ttggcaacat atgcccatat gtaactagca    1800
taaccccttg gggcctctaa cgggtcttg aggggttttt tgctgaaagc atgcggagga    1860
aattctcctt gaagtttccc tggtgttcaa agtaaaggag tttgcaccag acgcacctct    1920
gttcactggt ccggcgtatt aaaacacgat acattgttat tagtacattt attaagcgct    1980
agattctgtg cgttgttgat ttacagacaa ttgttgtacg tatttttaata attcattaaa    2040
tttataatct ttagggtggt atgttagagc gaaaatcaaa tgattttcag cgtctttata    2100
tctgaattta aatattaaat cctcaataga tttgtaaaat aggtttcgat tagtttcaaa    2160
caagggttgt ttttccgaac cgatggctgg actatctaat ggattttcgc tcaacgccac    2220
aaaacttgcc aaatcttgta gcagcaatct agctttgtcg atattcgttt gtgttttgtt    2280
ttgtaataaa ggttcgacgt cgttcaaaat attatgcgct tttgtatttc tttcatcact    2340
gtcgttagtg tacaattgac tcgacgtaaa cacgttaaat agagcttgga catatttaac    2400
atcgggcgtt ttagctttat taggccgatt atcgtcgtcg tcccaaccct cgtcgttaga    2460
agttgcttcc gaagacgatt tgccatagc cacacgacgc ctattaattg tgtcggctaa    2520
cacgtccgcg atcaaatttg tagttgagct ttttggaatt attctgattg cgggcgttt    2580
ttgggcgggt ttcaatctaa ctgtgcccga ttttaattca gacaacacgt tagaaagcga    2640
tggtgcaggg ggtggtaaca tttcagacgg caaatctact aatggcggcg gtggtggagc    2700
tgatgataaa tctaccatcg gtggaggcgc aggcggggct ggcggcggag gcggaggcgg    2760
aggtggtggc ggtgatgcag acggcggttt aggctcaaat gtctctttag caacacagt    2820
cggcacctca actattgtac tggtttcggg cgccgttttt ggtttgaccg gtctgagacg    2880
agtgcgattt ttttcgtttc taatagcttc caacaattgt tgtctgtcgt ctaaaggtgc    2940
agcgggttga ggttccgtcg gcattggtgg agcggcggc aattcagaca tcgatggtgg    3000
tggtggtggt ggaggcgctg gaatgttagg cacgggagaa ggtggtggcg gcggtgccgc    3060
cggtataatt tgttctggtt tagtttgttc gcgcacgatt gtgggcaccg gcgcaggcgc    3120
cgctggctgc acaacggaag gtcgtctgct tcgaggcagc gcttggggtg gtggcaattc    3180
aatattataa ttggaataca aatcgtaaaa atctgctata agcattgtaa tttcgctatc    3240
gtttaccgtg ccgatattta acaaccgctc aatgtaagca attgtattgt aaagagattg    3300
tctcaagctc ggaacgctgc gctcggtcgt tcggctgcgg cgagcggtat cagctcactc    3360
aaaggcggta atacggttat ccacagaatc aggggataac gcaggaaaga acatgtgagc    3420
aaaaggccag caaaaggcca ggaaccgtaa aaaggccgcg ttgctggcgt ttttccatag    3480
```

```
gctccgcccc cctgacgagc atcacaaaaa tcgacgctca agtcagaggt ggcgaaaccc    3540
gacaggacta taaagatacc aggcgtttcc ccctggaagc tccctcgtgc gctctcctgt    3600
tccgaccctg ccgcttaccg gatacctgtc cgcctttctc ccttcgggaa gcgtggcgct    3660
ttctcaatgc tcacgctgta ggtatctcag ttcggtgtag gtcgttcgct ccaagctggg    3720
ctgtgtgcac gaaccccccg ttcagcccga ccgctgcgcc ttatccggta actatcgtct    3780
tgagtccaac ccgtaagac acgacttatc gccactggca gcagccactg gtaacaggat    3840
tagcagagcg aggtatgtag gcggtgctac agagttcttg aagtggtggc ctaactacgg    3900
ctacactaga aggacagtat ttggtatctg cgctctgctg aagccagtta ccttcggaaa    3960
aagagttggt agctcttgat ccggcaaaca aaccaccgct ggtagcggtg gtttttttgt    4020
ttgcaagcag cagattacgc gcagaaaaaa aggatctcaa gaagatcctt tgttaccaat    4080
gcttaatcag tgaggcacct atctcagcga tctgtctatt tcgttcatcc atagttgcct    4140
gactccccgt cgtgtagata actacgatac gggagggctt accatctggc cccagtgctg    4200
caatgatacc gcgagaccca cgctcaccgg ctccagattt atcagcaata aaccagccag    4260
ccggaagggc cgagcgcaga agtggtcctg caactttatc cgcctccatc cagtctatta    4320
attgttgccg ggaagctaga gtaagtagtt cgccagttaa tagtttgcgc aacgttgttg    4380
ccattgctac aggcatcgtg gtgtcacgct cgtcgtttgg tatggcttca ttcagctccg    4440
gttcccaacg atcaaggcga gttacatgat cccccatgtt gtgcaaaaaa gcggttagct    4500
ccttcggtcc tccgatcgtt gtcagaagta agttggccgc agtgttatca ctcatggtta    4560
tggcagcact gcataattct cttactgtca tgccatccgt aagatgcttt tctgtgactg    4620
gtgagtactc aaccaagtca ttctgagaat agtgtatgcg gcgaccgagt tgctcttgcc    4680
cggcgtcaat acgggataat accgcgccac atagcagaac tttaaaagtg ctcatcattg    4740
gaaaacgttc ttcggggcga aaactctcaa ggatcttacc gctgttgaga tccagttcga    4800
tgtaacccac tcgtgcaccc aactgatctt cagcatcttt tactttcacc agcgtttctg    4860
ggtgagcaaa aacaggaagg caaaatgccg caaaaaaggg aataagggcg acacggaaat    4920
gttgaatact catactcttc cttttcaat attattgaag catttatcag ggttattgtc    4980
tcatgtccgc cgtttcctg catcttttaa tcaaatccca agatgtgtat aaaccaccaa    5040
actgccaaaa aatgaaaact gtcgacaagc tctgtccgtt tgctggcaac tgcaagggtc    5100
tcaatcctat ttgtaattat tgaataataa aacaattata aatgtcaaat tgttttttta    5160
ttaacgatac aaaccaaacg caacaagaac atttgtagta ttatctataa ttgaaaacgc    5220
gtagttataa tcgctgaggt aatatttaaa atcatttcca aatgattcac agttaatttg    5280
cgacaatata attttatttt cacataaact agacgccttg tcgtcttctt cttcgtattc    5340 cttctcttttt tcattttct cttcataaaa attaacatag ttattatcgt atccatatat    5400
gtatctatcg tatagagtaa attttttgtt gtcataaata tatatgtctt ttttaatggg    5460
gtgtatagta ccgctgcgca tagttttct gtaatttaca acagtgctat tttctggtag    5520
ttcttcggag tgtgttgctt taattattaa atttatataa tcaatgaatt tgggatcgtc    5580
ggttttgtac aatatgttgc cggcatagta cgcagcttct tctagttcaa ttacaccatt    5640
ttttagcagc accggattaa cataactttc caaaatgttg tacgaaccgt aaacaaaaaa    5700
cagttcacct ccctttttcta tactattgtc tgcgagcagt tgtttgttgt aaaaataaac    5760
agccattgta atgagacgca caaactaata tcacaaactg gaaatgtcta tcaatatata    5820
```

```
gttgctctag ttattaatag taatcaatta cggggtcatt agttcatagc ccatatatgg    5880
agttccgcgt tacataactt acggtaaatg gcccgcctgg ctgaccgccc aacgacccc     5940 gcccattgac gtcaataatg acgtatgttc ccatagtaac gccaataggg actttccatt    6000
gacgtcaatg ggtggactat ttacggtaaa ctgcccactt ggcagtacat caagtgtatc    6060
atatgccaag tacgccccct attgacgtca atgacggtaa atggcccgcc tggcattatg    6120
cccagtacat gaccttatgg gactttccta cttggcagta catctacgta ttagtcatcg    6180
ctattaccat gcatggtcga ggtgagcccc acgttctgct tcactctccc catctccccc    6240
ccctccccac ccccaatttt gtatttattt attttttaat tattttgtgc agcgatgggg    6300 gcggggggg gggggggcg cgcgccaggc ggggcgggc ggggcgaggg gcgggcggg        6360 gcgaggcgga gaggtgcggc ggcagccaat cagagcggcg cgctccgaaa gtttcctttt    6420
atggcgaggc ggcggcggcg gcggcccta t aaaaagcgaa gcgcgcggcg ggcgggagtc   6480
gctgcgacgc tgccttcgcc ccgtgccccg ctccgccgcc gcctcgcgcc gcccgccccg    6540
gctctgactg accgcgttac tcccacaggt gagcgggcgg gacggccctt ctccttcggg    6600
ctgtaattag cgcttggttt aatgacggct tgtttctttt ctgtggctgc gtgaaagcct    6660 tgagggctc cggggaggcc ctttgtgcgg ggggagcggc tcgggctgt ccgcgggggg     6720 acggctgcct tcggggggga cggggcaggg cggggttcgg cttctggcgt gtgaccggcg    6780
gctctagagc ctctgctaac catgttcatg ccttcttctt tttcctacag ctcctgggca    6840
acgtgctggt tattgtgctg tctcatcatt ttggcaaaga attggatcgg accgaaat     6898
```

<210> SEQ ID NO 6
<211> LENGTH: 438
<212> TYPE: PRT
<213> ORGANISM: Artificial Sequence
<220> FEATURE:
<223> OTHER INFORMATION: Flotillin-2[human]-His

<400> SEQUENCE: 6

```
Met Gly Asn Cys His Thr Val Gly Pro Asn Glu Ala Leu Val Val Ser
1               5                   10                  15

Gly Gly Cys Cys Gly Ser Asp Tyr Lys Gln Tyr Val Phe Gly Gly Trp
            20                  25                  30

Ala Trp Ala Trp Trp Cys Ile Ser Asp Thr Gln Arg Ile Ser Leu Glu
        35                  40                  45

Ile Met Thr Leu Gln Pro Arg Cys Glu Asp Val Glu Thr Ala Glu Gly
    50                  55                  60

Val Ala Leu Thr Val Thr Gly Val Ala Gln Val Lys Ile Met Thr Glu
65                  70                  75                  80

Lys Glu Leu Leu Ala Val Ala Cys Glu Gln Phe Leu Gly Lys Asn Val
                85                  90                  95

Gln Asp Ile Lys Asn Val Val Leu Gln Thr Leu Glu Gly His Leu Arg
            100                 105                 110

Ser Ile Leu Gly Thr Leu Thr Val Glu Gln Ile Tyr Gln Asp Arg Asp
        115                 120                 125

Gln Phe Ala Lys Leu Val Arg Glu Val Ala Ala Pro Asp Val Gly Arg
    130                 135                 140

Met Gly Ile Glu Ile Leu Ser Phe Thr Ile Lys Asp Val Tyr Asp Lys
145                 150                 155                 160

Val Asp Tyr Leu Ser Ser Leu Gly Lys Thr Gln Thr Ala Val Val Gln
                165                 170                 175
```

Arg Asp Ala Asp Ile Gly Val Ala Glu Ala Glu Arg Asp Ala Gly Ile
            180                 185                 190

Arg Glu Ala Glu Cys Lys Lys Glu Met Leu Asp Val Lys Phe Met Ala
        195                 200                 205

Asp Thr Lys Ile Ala Asp Ser Lys Arg Ala Phe Glu Leu Gln Lys Ser
    210                 215                 220

Ala Phe Ser Glu Glu Val Asn Ile Lys Thr Ala Glu Ala Gln Leu Ala
225                 230                 235                 240

Tyr Glu Leu Gln Gly Ala Arg Glu Gln Gln Lys Ile Arg Gln Glu Glu
                245                 250                 255

Ile Glu Ile Glu Val Val Gln Arg Lys Lys Gln Ile Ala Val Glu Ala
            260                 265                 270

Gln Glu Ile Leu Arg Thr Asp Lys Glu Leu Ile Ala Thr Val Arg Arg
        275                 280                 285

Pro Ala Glu Ala Glu Ala His Arg Ile Gln Gln Ile Ala Glu Gly Glu
    290                 295                 300

Lys Val Lys Gln Val Leu Leu Ala Gln Ala Glu Ala Glu Lys Ile Arg
305                 310                 315                 320

Lys Ile Gly Glu Ala Glu Ala Val Ile Glu Ala Met Gly Lys Ala
                325                 330                 335

Glu Ala Glu Arg Met Lys Leu Lys Ala Glu Ala Tyr Gln Lys Tyr Gly
            340                 345                 350

Asp Ala Ala Lys Met Ala Leu Val Leu Glu Ala Leu Pro Gln Ile Ala
        355                 360                 365

Ala Lys Ile Ala Ala Pro Leu Thr Lys Val Asp Glu Ile Val Val Leu
    370                 375                 380

Ser Gly Asp Asn Ser Lys Val Thr Ser Glu Val Asn Arg Leu Leu Ala
385                 390                 395                 400

Glu Leu Pro Ala Ser Val His Ala Leu Thr Gly Val Asp Leu Ser Lys
                405                 410                 415

Ile Pro Leu Ile Lys Lys Ala Thr Gly Val Gln Val Ile Glu His His
            420                 425                 430

His His His His His
        435

<210> SEQ ID NO 7
<211> LENGTH: 6900
<212> TYPE: DNA
<213> ORGANISM: Artificial Sequence
<220> FEATURE:
<223> OTHER INFORMATION: pTriEx-1-Flotillin-2[human]

<400> SEQUENCE: 7
taatacgact cactataggg gaattgtgag cggataacaa ttcccgggag ttaatccggg      60
acctttaatt caacccaaca caatatatta tagttaaata agaattatta tcaaatcatt     120
tgtatattaa ttaaaatact atactgtaaa ttacatttta tttacaatca aggagatat      180 accatgggca attgccacac ggtgggcccc aacgaggcac tggtggtctc aggggctgt      240 tgtggttctg actacaagca gtatgtgttt ggcggctggg cttgggcctg gtggtgtatc    300
tcggacactc agaggatttc cctagagatt atgacgttgc agccccgctg tgaggacgta     360 agacggccg aggggtagc tttaactgtg acgggtgtcg cccaggtgaa gatcatgacg      420
gagaaggagc tcctggctgt agcctgtgaa cagttcctgg caagaacgt gcaggacatt      480 aagaacgtcg tactgcagac cctggagggg catctacgct ccatccttgg gactctgact     540

```
gtggagcaga tttatcagga ccgagaccag tttgccaagc tggtgcggga agtggcagcc      600
cctgatgttg gccgtatggg catcgagatc ctcagcttca ccatcaagga tgtctatgac      660
aaagtagact atctgagctc cctgggcaag acacagactg ccgtggtaca gagagatgca      720
gacatcggtg tggcagaggc agagcgggac gcaggcatcc gggaagccga gtgcaagaag      780
gaaatgctag atgtgaagtt catggcagac accaagattg ctgactccaa gagagccttt      840
gagctgcaaa agtcagcctt cagtgaggag gtcaacatca agacagctga ggcccagttg      900
gcctatgagc tacaagggc cagagagcaa cagaagatcc ggcaggaaga gattgagatt       960
gaggtagtac agcgcaagaa gcagatcgcc gtggaggcgc aggagatcct gcgcacagac      1020
aaggagctca tcgccacagt gcgccgccct gcagaggcag aggcccaccg catccagcag      1080
attgctgaag gcgaaaaggt gaaacaagtc ctcttggcac aagcagaagc tgagaagatt      1140
cgcaaaatcg gggaggcaga ggcagcagtc attgaggcca tgggcaaggc cgaggccgag      1200
cggatgaagc ttaaagctga ggcctaccag aagtacgggg atgcggccaa gatggccctg      1260
gtgctggagg ccctgcccca gattgctgcc aagatcgccg caccctgac taaagtcgat       1320 gagattgtgg ttctcagtgg ggacaacagc aaggtgacat cagaagtgaa ccggctgcta      1380
gcagaactgc ctgcttctgt tcatgccctc actggtgtgg acctctcaaa gataccactg      1440
atcaagaaag ccactggtgt gcaggtgtaa tcgagcacca ccatcaccat caccatcact      1500
aagtgattaa cctcaggtgc aggctgccta tcagaaggtg gtggctggtg tggccaatgc      1560
cctggctcac aaataccact gagatcgatc ttttccctc tgccaaaaat tatggggaca       1620
tcatgaagcc ccttgagcat ctgacttctg gctaataaag gaaatttatt ttcattgcaa      1680
tagtgtgttg gaattttttg tgtctctcac tcggaaggac atatgggagg gcaaatcatt      1740
taaaacatca gaatgagtat ttggtttaga gtttggcaac atatgcccat atgtaactag      1800
cataacccct tggggcctct aaacgggtct tgaggggttt tttgctgaaa gcatgcggag      1860
gaaattctcc ttgaagtttc cctggtgttc aaagtaaagg agtttgcacc agacgcacct      1920
ctgttcactg gtccggcgta ttaaaacacg atacattgtt attagtacat ttattaagcg      1980
ctagattctg tgcgttgttg atttacagac aattgttgta cgtattttaa taattcatta      2040
aatttataat ctttagggtg gtatgttaga gcgaaaatca aatgattttc agcgtcttta      2100
tatctgaatt taaatattaa atcctcaata gatttgtaaa ataggtttcg attagtttca      2160
aacaagggtt gtttttccga accgatggct ggactatcta atggattttc gctcaacgcc      2220
acaaaacttg ccaaatcttg tagcagcaat ctagctttgt cgatattcgt ttgtgttttg      2280
ttttgtaata aaggttcgac gtcgttcaaa atattatgcg cttttgtatt tctttcatca      2340
ctgtcgttag tgtacaattg actcgacgta aacacgttaa atagagcttg gacatatta     2400 acatcgggcg tgttagcttt attaggccga ttatcgtcgt cgtcccaacc ctcgtcgtta      2460
gaagttgctt ccgaagacga ttttgccata gccacgcgac gcctattaat tgtgtcggct      2520
aacacgtccg cgatcaaatt tgtagttgag cttttttggaa ttatttctga ttgcgggcgt    2580 tttttgggcgg gtttcaatct aactgtgccc gattttaatt cagacaacac gttagaaagc    2640
gatggtgcag gcggtggtaa catttcagac ggcaaatcta ctaatggcgg cggtggtgga    2700
gctgatgata aatctaccat cggtggaggc gcaggcgggg ctggcggcgg aggcggaggc    2760
ggaggtggtg gcggtgatgc agacggcggt ttaggctcaa atgtctcttt aggcaacaca    2820
gtcggcacct caactattgt actggtttcg ggcgccgttt ttggtttgac cggtctgaga    2880
cgagtgcgat ttttttcgtt tctaatagct tccaacaatt gttgtctgtc gtctaaaggt    2940
```

```
gcagcgggtt gaggttccgt cggcattggt ggagcgggcg gcaattcaga catcgatggt    3000
ggtggtggtg gtggaggcgc tggaatgtta ggcacgggag aaggtggtgg cggcggtgcc    3060
gccggtataa tttgttctgg tttagtttgt tcgcgcacga ttgtgggcac cggcgcaggc    3120
gccgctggct gcacaacgga aggtcgtctg cttcgaggca gcgcttgggg tggtggcaat    3180
tcaatattat aattggaata caaatcgtaa aaatctgcta taagcattgt aatttcgcta    3240
tcgtttaccg tgccgatatt taacaaccgc tcaatgtaag caattgtatt gtaaagagat    3300
tgtctcaagc tcggaacgct gcgctcggtc gttcggctgc ggcgagcggt atcagctcac    3360
tcaaaggcgg taatacggtt atccacagaa tcagggaata cgcaggaaaa gaacatgtga    3420
gcaaaaggcc agcaaaaggc caggaaccgt aaaaaggccg cgttgctggc gttttcccat    3480
aggctccgcc cccctgacga gcatcacaaa aatcgacgct caagtcagag gtggcgaaac    3540
ccgacaggac tataaagata ccaggcgttt ccccctggaa gctccctcgt gcgctctcct    3600
gttccgaccc tgccgcttac cggatacctg tccgcctttc tcccttcggg aagcgtggcg    3660
ctttctcaat gctcacgctg taggtatctc agttcggtgt aggtcgttcg ctccaagctg    3720
ggctgtgtgc acgaaccccc cgttcagccc gaccgctgcg ccttatccgg taactatcgt    3780
cttgagtcca acccggtaag acacgactta tcgccactgg cagcagccac tggtaacagg    3840
attagcagag cgaggtatgt aggcggtgct acagagttct tgaagtggtg cctaactac    3900 ggctacacta aaggacagt atttggtatc tgcgctctgc tgaagccagt taccttcgga    3960
aaaagagttg gtagctcttg atccggcaaa caaaccaccg ctggtagcgg tggtttttt    4020 gtttgcaagc agcagattac gcgcagaaaa aaaggatctc aagaagatcc tttgttacca    4080
atgcttaatc agtgaggcac ctatctcagc gatctgtcta tttcgttcat ccatagttgc    4140
ctgactcccc gtcgtgtaga taactacgat acgggagggc ttaccatctg gccccagtgc    4200
tgcaatgata ccgcgagacc cacgctcacc ggctccagat ttatcagcaa taaaccagcc    4260
agccggaagg gccgagcgca gaagtggtcc tgcaacttta tccgcctcca tccagtctat    4320
taattgttgc cgggaagcta gagtaagtag ttcgccagtt aatagtttgc gcaacgttgt    4380
tgccattgct acaggcatcg tggtgtcacg ctcgtcgttt ggtatggctt cattcagctc    4440
cggttcccaa cgatcaaggc gagttacatg atccccatg ttgtgcaaaa aagcggttag    4500
ctccttcggt cctccgatcg ttgtcagaag taagttggcc gcagtgttat cactcatggt    4560
tatggcagca ctgcataatt ctcttactgt catgccatcc gtaagatgct tttctgtgac    4620
tggtgagtac tcaaccaagt cattctgaga atagtgtatg cggcgaccga gttgctcttg    4680
cccggcgtca atacgggata ataccgcgcc acatagcaga actttaaaag tgctcatcat    4740
tggaaaacgt tcttcgggc gaaaactctc aaggatctta ccgctgttga atccagttc    4800 gatgtaaccc actcgtgcac ccaactgatc ttcagcatct tttactttca ccagcgtttc    4860
tgggtgagca aaaacaggaa ggcaaaatgc cgcaaaaaag gaataagggg cgacacggaa    4920
atgttgaata ctcatactct tcctttttca atattattga agcatttatc agggttattg    4980
tctcatgtcc gcgcgtttcc tgcatctttt aatcaaatcc caagatgtgt ataaaccacc    5040
aaactgccaa aaatgaaaa ctgtcgacaa gctctgtccg tttgctggca actgcaaggg    5100
tctcaatcct atttgtaatt attgaataat aaaacaatta taaatgtcaa atttgttttt    5160
tattaacgat acaaaccaaa cgcaacaaga acatttgtag tattatctat aattgaaaac    5220
gcgtagttat aatcgctgag gtaatatttta aaatcatttt caaatgattc acagttaatt    5280
```

```
tgcgacaata taatttttatt ttcacataaa ctagacgcct tgtcgtcttc ttcttcgtat    5340
tccttctctt tttcatttttt ctcttcataa aaattaacat agttattatc gtatccatat    5400
atgtatctat cgtatagagt aaattttttg ttgtcataaa tatatatgtc ttttttaatg    5460
gggtgtatag taccgctgcg catagttttt ctgtaattta caacagtgct attttctggt    5520
agttcttcgg agtgtgttgc tttaattatt aaatttatat aatcaatgaa tttgggatcg    5580
tcggttttgt acaatatgtt gccggcatag tacgcagctt cttctagttc aattaccaca    5640 tttttttagca gcaccggatt aacataactt tccaaaatgt tgtacgaacc gttaaacaaa    5700
aacagttcac ctccctttc tatactattg tctgcgagca gttgtttgtt gttaaaaata    5760
acagccattg taatgagacg cacaaactaa tatcacaaac tggaaatgtc tatcaatata    5820
tagttgctct agttattaat agtaatcaat tacggggtca ttagttcata gcccatatat    5880
ggagttccgc gttacataac ttacggtaaa tggcccgcct ggctgaccgc ccaacgaccc    5940
ccgcccattg acgtcaataa tgacgtatgt tcccatagta acgccaatag ggactttcca    6000
ttgacgtcaa tgggtggact atttacggta aactgcccac ttggcagtac atcaagtgta    6060
tcatatgcca agtacgcccc ctattgacgt caatgacggt aaatggcccg cctggcatta    6120
tgcccagtac atgaccttat gggactttcc tacttggcag tacatctacg tattagtcat    6180
cgctattacc atgcatggtc gaggtgagcc ccacgttctg cttcactctc cccatctccc    6240 cccctccc acccccaatt ttgtatttat ttatttttta attattttgt gcagcgatgg    6300
gggcgggggg ggggggggg cgcgcgccag gcggggcggg gcggggcgag gggcggggcg    6360
gggcgaggcg gagaggtgcg gcggcagcca atcagagcgg cgcgctccga aagtttcctt    6420
ttatggcgag gcggcggcgg cggcggccct ataaaaagcg aagcgcgcgg cgggcgggag    6480
tcgctgcgac gctgccttcg ccccgtgccc cgctccgccg ccgcctcgcg ccgcccgccc    6540
cggctctgac tgaccgcgtt actcccacag gtgagcgggc gggacggccc ttctccttcg    6600
ggctgtaatt agcgcttggt ttaatgacgg cttgtttctt ttctgtggct gcgtgaaagc    6660 cttgagggc tccgggaggg ccctttgtgc gggggagcg gctcggggct gtccgcgggg    6720
ggacggctgc cttcgggggg gacggggcag ggcggggttc ggcttctggc gtgtgaccgg    6780
cggctctaga gcctctgcta accatgttca tgccttcttc ttttccctac agctcctggg    6840
caacgtgctg gttattgtgc tgtctcatca ttttggcaaa gaattggatc ggaccgaaat    6900
```

<210> SEQ ID NO 8
<211> LENGTH: 428
<212> TYPE: PRT
<213> ORGANISM: Homo sapiens

<400> SEQUENCE: 8

```
Met Gly Asn Cys His Thr Val Gly Pro Asn Glu Ala Leu Val Val Ser
1               5                   10                  15

Gly Gly Cys Cys Gly Ser Asp Tyr Lys Gln Tyr Val Phe Gly Gly Trp
            20                  25                  30

Ala Trp Ala Trp Trp Cys Ile Ser Asp Thr Gln Arg Ile Ser Leu Glu
        35                  40                  45

Ile Met Thr Leu Gln Pro Arg Cys Glu Asp Val Glu Thr Ala Glu Gly
    50                  55                  60

Val Ala Leu Thr Val Thr Gly Val Ala Gln Val Lys Ile Met Thr Glu
65                  70                  75                  80

Lys Glu Leu Leu Ala Val Ala Cys Glu Gln Phe Leu Gly Lys Asn Val
                85                  90                  95
```

-continued

```
Gln Asp Ile Lys Asn Val Val Leu Gln Thr Leu Glu Gly His Leu Arg
            100                 105                 110

Ser Ile Leu Gly Thr Leu Thr Val Glu Gln Ile Tyr Gln Asp Arg Asp
            115                 120                 125

Gln Phe Ala Lys Leu Val Arg Glu Val Ala Ala Pro Asp Val Gly Arg
            130                 135                 140

Met Gly Ile Glu Ile Leu Ser Phe Thr Ile Lys Asp Val Tyr Asp Lys
145                 150                 155                 160

Val Asp Tyr Leu Ser Ser Leu Gly Lys Thr Gln Thr Ala Val Val Gln
                165                 170                 175

Arg Asp Ala Asp Ile Gly Val Ala Glu Ala Glu Arg Asp Ala Gly Ile
                180                 185                 190

Arg Glu Ala Glu Cys Lys Lys Glu Met Leu Asp Val Lys Phe Met Ala
            195                 200                 205

Asp Thr Lys Ile Ala Asp Ser Lys Arg Ala Phe Glu Leu Gln Lys Ser
            210                 215                 220

Ala Phe Ser Glu Glu Val Asn Ile Lys Thr Ala Glu Ala Gln Leu Ala
225                 230                 235                 240

Tyr Glu Leu Gln Gly Ala Arg Glu Gln Gln Lys Ile Arg Gln Glu Glu
                245                 250                 255

Ile Glu Ile Glu Val Val Gln Arg Lys Lys Gln Ile Ala Val Glu Ala
            260                 265                 270

Gln Glu Ile Leu Arg Thr Asp Lys Glu Leu Ile Ala Thr Val Arg Arg
            275                 280                 285

Pro Ala Glu Ala Glu Ala His Arg Ile Gln Gln Ile Ala Glu Gly Glu
            290                 295                 300

Lys Val Lys Gln Val Leu Leu Ala Gln Ala Glu Ala Glu Lys Ile Arg
305                 310                 315                 320

Lys Ile Gly Glu Ala Glu Ala Val Ile Glu Ala Met Gly Lys Ala
            325                 330                 335

Glu Ala Glu Arg Met Lys Leu Lys Ala Glu Ala Tyr Gln Lys Tyr Gly
            340                 345                 350

Asp Ala Ala Lys Met Ala Leu Val Leu Glu Ala Leu Pro Gln Ile Ala
            355                 360                 365

Ala Lys Ile Ala Ala Pro Leu Thr Lys Val Asp Glu Ile Val Val Leu
            370                 375                 380

Ser Gly Asp Asn Ser Lys Val Thr Ser Glu Val Asn Arg Leu Leu Ala
385                 390                 395                 400

Glu Leu Pro Ala Ser Val His Ala Leu Thr Gly Val Asp Leu Ser Lys
                405                 410                 415

Ile Pro Leu Ile Lys Lys Ala Thr Gly Val Gln Val
            420                 425
```

DIAGNOSIS OF A NEUROAUTOIMMUNE DISEASE COMPRISING MEASURING AUTOANTIBODIES TO FLOTILLIN1 AND/OR FLOTILLIN2

BACKGROUND OF THE INVENTION

Field of the Invention

The present invention relates to a method for diagnosing a disease comprising detecting in a sample from a patient an autoantibody binding to flotillin1 and/or flotillin2, a polypeptide comprising flotillin1 and/or flotillin2 or a variant thereof, which is may be immobilized, use of the polypeptide for the diagnosis of a disease, an autoantibody binding to flotillin1 and/or flotillin2, a method for isolating said autoantibody, and a pharmaceutical composition, medical device, and/or test kit comprising said polypeptide.

Discussion of the Background

Developing diagnostic systems for neurological diseases is a continuing challenge in biomedical science, not in the least because many encountered symptoms may be accounted for by a huge variety of causes including genetically inherited diseases, drug abuse, malnutrition, infection, injury, psychiatric illness, immunological defects, and cancer.

Since a neurological disease is rarely associated with a unique characteristic pattern of clinical symptoms, it is often difficult to provide a reliable diagnosis solely based on the observation and examination of the patients affected or their medical history.

The importance of an early diagnosis cannot be overemphasized. Many neurological disorders, most prominently Alzheimer's and Parkinson's diseases as well as Multiple Sclerosis, cannot be cured, but drugs are available that may be used to slow down their progression. The earlier a patient is diagnosed, the better chances to exploit a spectrum of available drugs to the full benefit of the patient.

This holds all the more true in the case of neurological diseases associated with autoantibodies. In some cases, a link between a specific detectable autoantibody and a condition is sufficiently strong to allow for immediate diagnosis.

But even if it is not, detection of autoantibodies may point a physician in charge to therapeutic means that may be used to ameliorate patient's conditions. There is a variety of widely used immunosuppressants that may be used regardless of the nature of the autoantibody's target. Alternatively, apheresis may be used to remove autoantibodies from patient's blood. In many cases, patients could live a normal life following early diagnosis and treatment of a neurological autoimmune disease.

Diagnostic assays based on the detection of autoantibodies may also corroborate the diagnosis of diseases other than those associated with autoantibodies. If it turns out that a blood sample is devoid of specific autoantibodies, this is likely to help a physician in charge to exclude a range of possibilities and thus narrow down the spectrum of plausible conditions.

Examples of neurological conditions coinciding with the emergence of autoantibodies include Neuromyelitis optica, a disease characterized by loss of vision and a spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such were previously poorly understood, many of these diseases may now be diagnosed and treated efficiently owing to the availability of assays based on the detection of autoantibodies.

Multiple Sclerosis is another disease that is widely believed to be associated with the autoimmune destruction of vital bodily structures. Approximately 20% of patients suffer from a visual impairment, more specifically optic neuritis. A specific diagnosis is difficult owing to a wide spectrum of symptoms and the nature of the disease, with attacks being followed sometimes by a complete disappearance of the symptoms.

Therefore, there still exists a need for better and more effective approaches to distinguish neurological conditions associated with autoantibodies.

SUMMARY OF THE INVENTION

The present invention relates to a method for diagnosing a disease comprising detecting in a sample from a patient an autoantibody binding to flotillin1 and/or flotillin2, a polypeptide comprising flotillin1 and/or flotillin2 or a variant thereof, which may be immobilized, use of the polypeptide for diagnosis of a disease, an autoantibody binding to flotillin1 and/or flotillin2, a method for isolating the autoantibody, and a pharmaceutical composition, a medical device, and a test kit comprising the polypeptide.

One object of the present invention is to providing novel reagents, devices and methods that may be used to support diagnosis and treatment of a neurological disease, in particular a disease associated with vision impartment, headache and/or brain lesions.

Another object of the present invention is to provide novel reagents, devices and methods that may be used to distinguish autoimmune diseases, in particular neurological autoimmune diseases, from diseases other than autoimmune diseases, not in the least to determine a promising treatment regimen, more specifically whether or not immunosuppressive treatment is adequate.

These and other objects of the present invention, which will become more apparent in conjunction with the following detailed description of the preferred embodiments, either alone or in combinations thereof, have been satisfied by the discovery of a method for diagnosing a disease comprising detecting in a sample from a patient an autoantibody that binds to flotillin1 and/or flotillin2.

A method of treating a disease, comprising applying the polypeptide that binds an autoantibody binding to flotillin1 and/or flotillin2 to a subject in need thereof, is further provided.

A further object of the invention is to provide an isolated autoantibody that binds to flotillin1 and/or flotillin2.

A still further object of the present invention is to provide a method for isolating an autoantibody that binds to flotillin1 and/or flotillin2, comprising:

a) contacting a sample comprising the autoantibody with the polypeptide according to claim 2 under conditions compatible with formation of a complex, wherein said autoantibody binds to said polypeptide,
b) isolating the complex formed in step a),
c) dissociating the complex isolated in step b), and
d) separating the autoantibody from the polypeptide.

A pharmaceutical composition comprising the polypeptide and a test kit for diagnosis of a disease, comprising the polypeptide and a means for detecting a complex comprising the polypeptide and an autoantibody that binds to flotillin1 and/or flotillin2, are provided.

Another object of the present invention is to provide a method for detecting the presence of an autoantibody in a sample, comprising exposing a polypeptide comprising at least one of flotillin1 and flotillin2 or a variant thereof, which may be immobilized on a solid carrier, to a sample from a subject and detecting the autoantibody which has bound to the polypeptide.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1: A, B, C, D show MM of the head demonstrating multiple demyelinating lesions in the anti-flotillin positive patient. T2 weighted magnetic resonance imaging (A, C), and flair imaging (B, D) of the same female 34 year old patient at initial presentation (A, B), and after 6 month (C, D).

FIG. 2: A, B, C show Immunofluorescence staining of central nervous tissues. A) Hippocampus rat, B) cerebellum rat, C) cerebellum monkey.

Figure 3A:
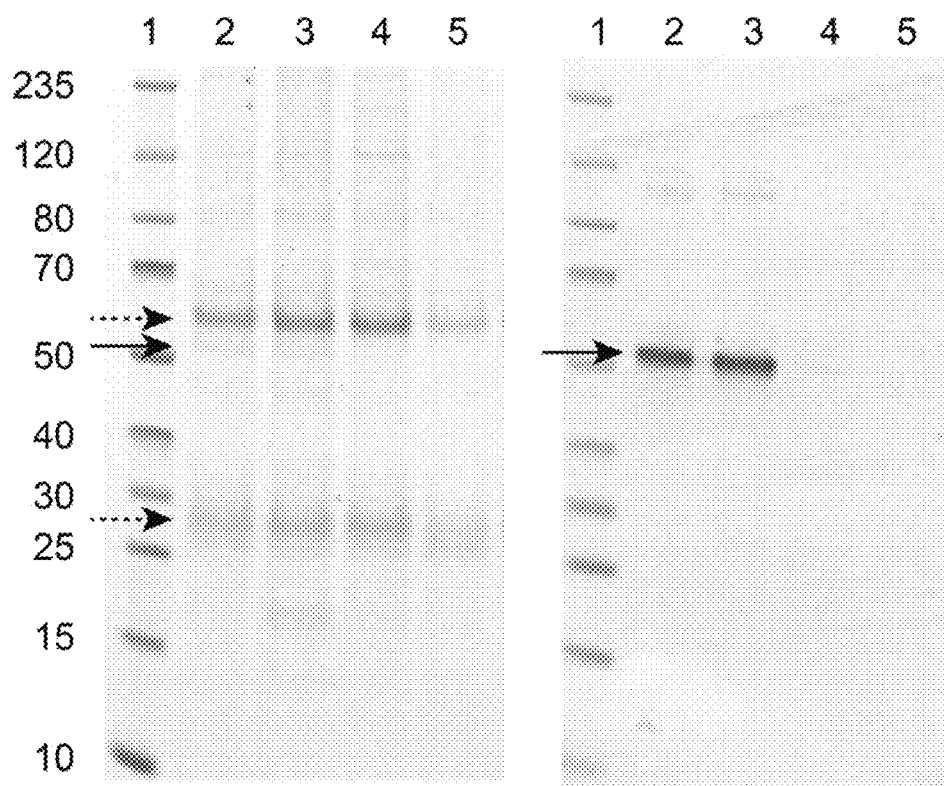
FIG. 3: A, B1-B12 show Histo-immunoprecipitation and antigen identification.

A) Left: Staining with colloidal Coomassie. Right: Western blot after incubation with anti-flotillin2. Lane 1: molecular weight marker, lane 2 & 3: histo-immunoprecipitates of patient's sera from rat cerebellum, lanes 4 & 5: histo-immunoprecipitates of control samples. The arrow indicates the position of the immunoprecipitated antigen 50 kDa while dotted arrows indicate the position of IgG heavy chain at 52 kDa.

B1-B12) Immunofluorescence staining of rat hippocampus (1-3) and cerebellum (4-6), monkey intestinal (7-9) and optic nerve (10-12) tissue sections with patient's serum (1 & 4) and anti-flotillin2 antibody (2 & 5). The merged pictures show co-localization of both reactivities including the more intense staining of the outer molecular layer on hippocampus (3 & 6).

FIG. 4: A1-A4, B1-B8 show immunofluorescence staining of recombinant flotillin and its neutralization of the antibody reaction on tissue.

A1-A4) Immunofluorescence analysis of transfected HEK293 cells. Patient or control sera (1:1000) (green) were incubated on acetone-fixed recombinant HEK293 cells expressing flotillin1 (A), flotillin2 (B), flotillin1 and -2 (C) or a mock-transfected control (D).

B1-B8) Neutralization of immunofluorescence reaction on neuronal tissues. Patient serum (green) was pre-incubated with extracts of HEK293 cells transfected with empty vector as control (1-4) or with flotillin1/2 (5-8). The extract containing flotillin1/2 greatly reduced or abolished the immune reaction. Nuclei were counterstained by incubation with TO-PRO-3 iodide (blue). Hippocampus rat (1 & 5), cerebellum rat (2 & 6), cerebellum monkey (3 & 7), HEK293-flotillin1/2 (4 & 8).

DETAILED DESCRIPTION OF THE INVENTION

All methods and materials similar or equivalent to those described herein can be used in the practice or testing of the present invention, with suitable methods and materials being described herein. All publications, patent applications, patents, and other references mentioned herein are incorporated by reference in their entirety.

Generally, the present invention provides a method for diagnosing a disease comprising detecting an autoantibody binding to flotillin1 and/or flotillin2 in a sample from a patient, a polypeptide, an autoantibody, a pharmaceutical composition, a medical device, and a test kit comprising the polypeptide.

A polypeptide comprising flotillin1 and/or flotillin2 or a variant thereof, which is preferably immobilized, and more preferably on a solid carrier, is provided.

In one embodiment, the polypeptide is used for diagnosis of a disease, preferably comprising detecting an autoantibody binding to flotillin1 and/or flotillin2 in a sample.

In a different embodiment, the polypeptide is used for treatment of a disease.

Another object of the present invention is to provide an autoantibody, preferably an isolated autoantibody, binding to flotillin1 and/or flotillin2, preferably to a complex comprising flotillin1 and flotillin2, wherein the autoantibody is preferably in complex with the provided polypeptide.

A different object of the present invention is to provide a method for isolating an autoantibody binding to flotillin1 and/or flotillin2, preferably a complex comprising flotillin1 and flotillin2, comprising:

a) contacting a sample comprising the autoantibody with a polypeptide under conditions compatible with the formation of a complex, wherein said autoantibody binds to said polypeptide,
b) isolating the complex formed in a),
c) dissociating the complex isolated in b), and
d) separating the autoantibody from the polypeptide.

The present invention further relates to a pharmaceutical composition or medical device, preferably a diagnostic device, comprising the polypeptide.

A different object of the present invention is to provide a test kit for the diagnosis of a disease, wherein the test kit comprises the polypeptide, and, preferably, a means for detecting a complex comprising the polypeptide and autoantibody binding to flotillin1 and/or flotillin2.

In one embodiment, a patient may have or a disease may be associated with one or more, preferably two or more symptoms selected from the group consisting of elevated cell number in CSF, intrathecal IgG synthesis, oligoclonal bands in CSF, MRZ (M-measles, R-rubella, Z-varicella zoster) reaction in CSF, impairment of vision, preferably impairment of visual acuity, optic neuritis, headache, spinal cord lesions and brain lesions, preferably impairment of vision, more preferably of visual acuity, headache, spinal cord lesions, and brain lesions.

In another embodiment, the disease is a neurological disease, preferably a demyelinating disease, preferably a disease of the CNS, preferably of the encephalon, preferably associated with inflammation of the optical nerve.

In a different embodiment, the polypeptide is provided in the form of a cell comprising a nucleic acid encoding said polypeptide or in the form of a tissue comprising said polypeptide.

In yet another embodiment, the polypeptide is a recombinant and/or isolated polypeptide.

In one embodiment, the sample is a bodily fluid comprising antibodies, preferably selected from the group consisting of whole-blood, serum, cerebrospinal fluid, and saliva.

In another embodiment, both a polypeptide comprising flotillin1 or a variant thereof and a polypeptide comprising flotillin2 or a variant thereof are present and preferably a part of the complex.

In one embodiment, an autoantibody binds to a complex comprising flotillin1 and flotillin2. In another embodiment, the autoantibody is in complex with a polypeptide comprising flotillin1 and/or flotillin2 or a variant thereof, which may be immobilized on a solid carrier.

The detecting may comprise applying the polypeptide that binds to the autoantibody.

The autoantibody could bind to a complex comprising flotillin1 and flotillin2.

Another object of the present invention is to provide a method for detecting the presence of an autoantibody in a sample, comprising exposing a polypeptide comprising at least one of flotillin1 and flotillin2 or a variant thereof, which may be immobilized on a solid carrier, to a sample from a subject and detecting the autoantibody which has bound to the polypeptide.

The inventors have surprisingly found that a neurological autoimmune disease exists that is associated with an autoantibody to flotillin1 and/or flotillin2 considering symptoms from the group consisting of elevated cell number in CSF, intrathecal IgG synthesis, oligoclonal bands in CSF, MRZ reaction in CSF, impairment of vision, optic neuritis, headache, spinal cord lesions, and brain lesions.

In one embodiment, the method of treating a disease is in a human.

In another embodiment, the polypeptide comprises the amino acid sequence of SEQ ID NO: 2, 4, 6, and/or 8 or comprises an amino acid sequence encoded by the nucleotide sequence of SEQ ID NO: 1, 3, 5, and/or 7.

Furthermore, the inventors have further surprisingly found that autoantibodies to flotillin1 and/or flotillin2 exist and may be detected in samples from a number of patients suffering from neurological symptoms, but not in samples obtained from healthy subjects.

Furthermore, the inventors have also surprisingly found that known neurological diseases of unknown etiology, in particular demyelinating diseases, are associated with the presence of an autoantibody to flotillin1 and/or flotillin2.

Without wishing to be bound to any theory, the presence of such autoantibodies suggests that the activity and/or function of flotillin1 and/or flotillin2 and/or downstream effectors is impaired in patients having such autoantibodies to the effect that neurological symptoms, more specifically demyelinating diseases, in particular those associated with visual important, occur.

Flotillin1 and -2 (synonyms: reggie-2 and -1) were originally found as being upregulated in regenerating axons of goldfish retinal ganglion cells after traumatic injury of the optic nerve. However, they are well conserved in many eukaryotes including mammals. In vertebrates, both proteins are ubiquitously expressed and most abundant in striated muscle, adipose tissue and lung tissues. On the molecular level, flotillins are attached to the cytoplasmic side of lipid rafts and are therefore often used as markers of lipid microdomains. Similar to other lipid raft constituents, they are largely insoluble in Triton X-100 but float after sucrose density centrifugation. Functionally, they are involved in protein interactions, cell signaling, clustering of the amyloid precursor protein and amyloidogenic processing in neurons (Stuermer C A, Plattner H. The 'lipid raft' microdomain proteins reggie-1 and reggie-2 (flotillins) are scaffolds for protein interaction and signalling. Biochem. Soc. Symp., 2005; (72):109-18). Overexpression of flotillin-2 is seen in several types of cancer and is generally associated with a more severe progression (Arkhipova K A, Sheyderman A N, Laktionov K K, Mochalnikova V V, Zborovskaya I B. Simultaneous expression of flotillin-1, flotillin-2, stomatin and caveolin-1 in non-small cell lung cancer and soft tissue sarcomas. BMC Cancer, 2014; 14:100).

One object of the present invention relates to a polypeptide comprising a mammalian, preferably human flotillin1 or variants thereof and/or flotillin2 or variants thereof, preferably immunogenic variants reactive to autoantibodies binding to flotillin1 and flotillin2 or variants thereof. Examples of mammalian flotillin1 and/or flotillin2 include those from human, monkey, mouse, rat, rabbit, guinea pig or pig. In a most preferred embodiment, flotillin1 is the polypeptide encoded by the data base code O75955 or a variant thereof and/or flotillin2 is the polypeptide encoded by the data base code Q14254 or a variant thereof. Throughout this application, any cited data base codes refer to the Uniprot data base, more specifically the version accessible on-line on May 29, 2015. NP_005794 and NP_004466 represent a nucleotide sequence encoding flotillin1 and flotillin2, respectively.

In a preferred embodiment, the polypeptide comprises both flotillin1 or a variant thereof and flotillin 2 or variants thereof, fused to each other directly or via a linker. In another preferred embodiment, a complex comprising both polypeptide comprising flotillin1 or a variant thereof and a polypeptide comprising flotillin 2 or a variant thereof, binding directly to each other or via another molecule is used. Preferably, the complex comprises no proteins other than a polypeptide comprising flotillin1 or a variant thereof and a polypeptide comprising flotillin 2 or a variant thereof. Such a complex may be used to capture autoantibodies binding to said complex for diagnosis of a disease.

If a complex comprising a first polypeptide comprising flotillin1 or a variant thereof and a second polypeptide comprising flotillin2 or a variant thereof is used, the first and the second polypeptide may be expressed in the same cell to form such a complex. Alternatively, the first and the second polypeptide may be expressed separately in different cells and reconstituted following expression, optionally in a purified form.

Objects of the present invention may not only be carried out by using polypeptides, in particular a polypeptide comprising the native sequence of flotillin1 and/or flotillin2, or nucleic acids having the exact sequences referred to in this application explicitly, for example by function, name, sequence or accession number, or implicitly, but also using variants of such polypeptides or nucleic acids.

The term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150, or 200 successive amino acids of the original sequence or a variant thereof. The total length of the variant may be at least 6, 7, 8, 9, 10, 11, 12, 20, 25, 30, 40, 50, 60, 70, 80, 90, 100 or more amino acids.

The term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or a fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The related art describes various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In one embodiment, a polypeptide and variants thereof may, in addition, comprise chemical modifications, for example isotopic labels or covalent modifications such as glycosylation, phosphorylation, acetylation, decarboxylation, citrullination, methylation, hydroxylation and the like. A person skilled in the art is familiar with the methods to modify polypeptides. Any modification is designed such that it does not abolish the biological activity of the variant.

Variants may also be generated by fusion with other polypeptides or variants thereof and comprise active portions or domains, preferably having a sequence identity of at least 70, 75, 80, 85, 90, 92, 94, 95, 96, 97, 98, or 99% when aligned with the active portion of a reference sequence, wherein the term "active portion", as used herein, refers to an amino acid sequence, which is less than the full length amino acid sequence or, in the case of a nucleic acid sequence, encodes for less than the full length amino acid sequence, respectively, and/or is a variant of the natural sequence, but retains at least some of the biological activities.

The term "variant" of a nucleic acid comprises nucleic acids the complementary strand of which hybridizes, preferably under stringent conditions, to the reference or wild type nucleic acid. Stringency of hybridization reactions could be determinable by one of ordinary skilled in the art, and in general is an empirical calculation and dependents on the probe length, washing temperature and salt concentration. In general, longer probes require higher temperatures for proper annealing, while shorter probes less so. Hybridization generally depends on the ability of denatured DNA to reanneal to complementary strands present in the environment below their melting temperature, wherein the higher a degree of desired homology between the probe and hybridizable sequence, the higher a relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, a person skilled in the art may follow instructions given in the manual Boehringer Mannheim GmbH (1993), The DIG System Users Guide for Filter Hybridization, Boehringer Mannheim GmbH, Mannheim, Germany and in Liebl, W., Ehrmann, M., Ludwig, W., and Schleifer, K. H. (1991), International Journal of Systematic Bacteriology 41: 255-260, on how to identify DNA sequences by means of hybridization. In one embodiment, stringent conditions are applied for any hybridization, i.e., hybridization occurs only if the probe is 70% or more identical to the target sequence. Probes having a lower degree of identity with respect to the target sequence may hybridize, but such hybrids may be unstable and could be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust a concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, or 99% may be isolated. In a preferred embodiment, the term "variant" of a nucleic acid sequence, as used herein, refers to any nucleic acid sequence that encodes the same amino acid sequence and variants thereof as the reference nucleic acid sequence, in line with the degeneracy of the genetic code.

A variant of the polypeptide has a biological activity. In one embodiment, such biological activity is the ability to bind specifically to an autoantibodies of interest, preferably those binding to flotillin1 and/or flotillin2 found in patients suffering from a disease identified by the inventors.

A polypeptide, which comprises flotillin1 and/or flotillin2 or a variant thereof, or an autoantibody, may be provided in any form and at any degree of purity, from liquid samples, tissues or cells comprising said polypeptide in an endogenous form, more preferably cells overexpressing the polypeptide, crude or enriched lysates of such cells, to a purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. Methods for engineering nucleic acids and encoded polypeptides are, for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides in, for example, Handbooks "Strategies for Protein Purification", "Antibody Purification", "Purifying Challenging Proteins" (2009/2010), published by GE Healthcare Life Sciences, and in Burgess, R. R., Deutscher, M. P. (2009), Guide to Protein Purification). In one embodiment, a polypeptide is pure if at least 60, 70, 80, 90, 95 or 99 percent of the polypeptide in the respective sample contains said polypeptide as judged by SDS polyacrylamide gel electrophoresis followed by Coomassie blue staining and visual inspection.

If the polypeptide is provided in the form of a tissue, it is preferred that the tissue is mammalian tissue, for example human, rat, primate, donkey, mouse, goat, horse, sheep, pig or cow, more preferably brain tissue, and most preferably cerebellum. If a cell lysate is used, it is preferred that the cell lysate comprises membranes associated with the surface of the cell. If said polypeptide is provided in the form of a recombinant cell, it is preferred that the recombinant cell is an eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig, or cow.

A polypeptide used to carry out objects of the present invention, including any variants, is preferably designed such that it comprises epitopes recognized by and/or binds specifically to autoantibodies binding to flotillin1 and/or flotillin2. In one embodiment, such polypeptide comprises a stretch of 6, 7, 8, 9, 10, 11, 12, 20, 25, 30, 40, 50, 60, 70, 80, 90, 100 or more, preferably at least 9 but no more than 16, consecutive amino acids from flotillin1 and/or flotillin2. Guidelines used to design peptides having sufficient immunogenicity could be found in, for example, Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group consisting of aspartate, proline, tyrosine, and phenylalanine, (c) is has, for higher specificity, no or little homology with other known peptides or polypeptides, (d) it needs to be sufficiently soluble, and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71.

A polypeptide that comprises flotillin1 and/or flotillin2 or a variant thereof, preferably one or a polypeptide or a complex of two or more polypeptides comprising flotillin1 and flotillin2, may be provided in any kind of conformation. For example, the polypeptide may be an essentially unfolded or a partially or fully folded polypeptide. In a preferred embodiment, the polypeptide is folded in the sense that the epitopes essential for the binding to the autoantibody, or the protein or variant thereof in its entirety, adopt the fold adopted by the native protein in its natural environment. Methods suitable to determine whether or not a polypeptide is folded and if it is, which structure it has, could be found in, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably CD spectroscopy is used.

A polypeptide may be a fusion protein which comprises amino acid sequences other than those taken from flotillin1 and/or flotillin2, in particular a C-terminal or N-terminal tag, preferably a C-terminal tag, which is, in a preferred embodiment, an additional sequence motif or polypeptide having a function that has some biological or physical function and may, for example, be used to purify, immobilize, precipitate or identify the polypeptide. In a more preferred embodiment, the tag is a sequence or domain capable of binding specifically to a ligand, for example, a tag selected from the group consisting of His tags, thioredoxin, maltose binding protein, glutathione-S-transferase, a fluorescence tag, for example, green fluorescent proteins. SEQ ID NOs: 1, 2 and SEQ ID NOs: 5, 6 represent exemplary fusion polypeptides comprising flotillin1 and flotillin2, or the nucleotide sequences encoding the polypeptides, respectively.

A polypeptide may be an immobilized polypeptide. In one embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Such a carrier is preferably an artificial carrier, which is not predominantly a biological material such as a tissue section. Various suitable carriers, for example, paper, polystyrene, metal, silicon or glass surfaces, microfluidic channels, membranes, beads such as magnetic beads, column chromatography media, biochips, polyacrylamide gels and the like are described in, for example, Kim, D., and Herr, A. E. (2013), Protein immobilizsation techniques for microfluidic assays, Biomicrofluidics 7(4), 041501. An immobilized molecule, together with an insoluble carrier, may be separated from an aqueous solution in a straightforward manner, for example, by filtration, centrifugation, or decanting. An immobilized molecule may be immobilized in a reversible or irreversible manner. For example, immobilization is reversible if the molecule interacts with a carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to a carrier via a covalent bond that cannot be cleaved in an aqueous solution, for example, a bond formed by the reaction of an epoxide group and an amine group as frequently used to couple lysine side chains to affinity columns. A protein may be indirectly immobilized, for example, by immobilizing an antibody or other entity having affinity to the molecule, followed by formation of a complex to the effect that the molecule-antibody complex is immobilized. Various ways to immobilize molecules are described in, for example, Kim, D., Herr, and A. E. (2013), Protein immobilizsation techniques for microfluidic assays, Biomicrofluidics 7(4), 041501. In addition, various reagents and kits for immobilization reactions are commercially available, for example, from Pierce Biotechnology.

A sample used for diagnosis comprises antibodies, also referred to as immunoglobulins. Typically, a sample of a bodily fluid comprises a representative set of the entirety of subject's immunoglobulins. However, the sample, once provided, may be subjected to a further processing which may include fractionation, centrifugation, enrichment, or isolation of the entirety of immunoglobulins or any immunoglobulin class of the subject, which may affect a relative distribution of the immunoglobulins of various classes.

Reagents, devices, methods, and applications described throughout this application may be used for diagnosing a disease. In one embodiment, the disease is a neurological disease. The term "neurological disease", as used herein, refers to any disease associated with a defect of the nervous system, more preferably an element of the nervous system essential for vision, more preferably the optical nerve.

In one embodiment, a disease, more preferably a neurological disease, is associated with one or more symptoms, more preferably two or more, most preferably three or more from the group consisting of cancer, elevated cell number in CSF, intrathecal IgG synthesis, oligoclonal bands in CSF, MRZ reaction in CSF, impairment of vision, preferably of visual acuity, optic neuritis, headache, spinal cord lesions and brain lesions. Preferably the disease is responsive to immunomodulatory, preferably immunosuppressive therapy.

In another embodiment, a disease is a neurological disease selected from the group consisting of Alzheimer's Disease, Autism, Aspergers's Syndrome, Apraxia, Aphasia, Cerebellar syndrome, Cerebellitis, Chorea, Encephalitis, Movement disorder, spinocerebellar ataxia, preferably a non-progressive form, Paralysis, Paraplegia, Gaucher's disease, Myopathy, Myasthenia gravis, Multiple Sclerosis, Parkinsons's disease, Polyneuropathy and Dementia, preferably Cerebellar syndrome, Cerebellitis, Multiple Sclerosis, Movement disorder and Dementia, more preferably Multiple Sclerosis. In another embodiment, a disease is a demyelinating disease, more preferably a demyelinating disease affecting the CNS, more preferably Multiple Sclerosis, and most preferably associated with optic neuritis.

In another embodiment, a disease is a cancer or, preferably the paraneoplastic neurological syndrome, which is associated both with one or more neurological symptoms, preferably from the group consisting of elevated cell number in CSF, intrathecal IgG synthesis, oligoclonal bands in CSF, MRZ reaction in CSF, impairment of vision, optic neuritis, headache, spinal cord lesions, and brain lesions and is furthermore associated with cancer. The detection of autoantibodies to flotillin1 and/or flotillin2 may indicate the increased likelihood that cancer is present which cannot be detected using other methods, or could appear as the disease progresses. In one embodiment, cancer is a cancer of tumor selected from the group consisting of lung tumor, thymus tumor, thymic tumor, testicular tumor, head and neck cancer tumor, breast cancer tumor, ano-genital cancer tumor, melanoma, sarcoma, carcinoma, lymphoma, leukemia, mesothelioma, glioma, germ cell tumor, choriocarcinoma, pancreatic cancer, ovarian cancer, gastric cancer, carcinomatous lesion of the pancreas, pulmonary adenocarcinoma, colorectal adenocarcinoma, pulmonary squamous adenocarcinoma, gastric adenocarcinoma, ovarian surface epithelial neoplasm (e.g. a benign, proliferative or malignant variety thereof), oral squamous cell carcinoma, non-small-cell lung carcinoma, endometrial carcinoma, a bladder cancer, prostate carcinoma, acute myelogenous leukemia (AML), myelodysplasia syndrome (MDS), non-small cell lung cancer (NSCLC), Wilms' tumor, leukemia, lymphoma, desmoplastic small round cell tumor, mesothelioma (e.g. malignant mesothelioma), a gastric cancer, colon cancer, lung cancer, breast cancer, germ cell tumor, ovarian cancer, uterine cancer, thyroid cancer, hepatocellular carcinoma, thyroid cancer, liver cancer, renal cancer, kaposis, sarcoma, and another carcinoma or sarcoma.

The term "diagnosis", as used herein, refers to any procedure aiming at obtaining information instrumental to the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of the patient with regard to a certain treatment, for example administration of immunosuppressive drugs. The term "diagnosis" comprises not only diagnosing, but also prognosticating and/or monitoring the course of a disease or disorder.

In many cases the detection, i.e., determining whether or not detectable levels of the antibody are present in a sample, is sufficient for diagnosis. If an autoantibody can be detected, this information could be instrumental for clinician's diagnosis and indicative of the increased likelihood that the patient suffers from a disease. In one embodiment, a relative concentration of the antibody in serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 0.1, preferably 0.2, 0.5, 1, 2, 5, 10, 20, 25, 50, 100, 200, 500, 1000, 10000 or 100000 times higher than the concentration found in the average healthy subject.

A clinician does not usually conclude whether or not a patient suffers or is likely to suffer from a disease, condition or disorder solely on the basis of a single diagnostic parameter, but needs to take into account other aspects, for example, the presence of other autoantibodies, markers, blood parameters, clinical assessment of patient's symptoms or results of medical imaging or other non-invasive methods such as polysomnography, to arrive at the conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In one embodiment, the provided polypeptide or method may be used to determine whether a patient suffers from a disease characterized by symptoms similar to those of MS, more preferably for the distinction between MS and NMO.

The term "diagnosis" does not imply that diagnostic methods or agents according to the present invention will be definitive and sufficient to finalize the diagnosis on the basis of a single test, let alone parameter, but may refer to a contribution to what is referred to as a "differential diagnosis", i.e., a systematic diagnostic procedure considering the likelihood of a range of possible conditions on the basis of a range of diagnostic parameters.

Consequently, the provided method, polypeptide, or application thereof, optionally for determining whether a patient suffers from a disease, may comprise obtaining a sample from the patient, preferably a human patient, determining whether an autoantibody binding to flotillin1 and/or flotillin2 is present in said sample, wherein said determining is performed by contacting the sample with the polypeptide and detecting whether binding occurs between said polypeptide and said autoantibody, preferably using a labeled secondary antibody, wherein said autoantibody binds to said polypeptide if present in the sample, and diagnosing the patient as suffering or being more likely to suffer from said neurological disorder or cancer if the autoantibody was determined to be present in the sample. In one embodiment, the method may contain detecting antibody to a) Aquaporin-4 and b) flotillin1 and/or -2, preferably in that order.

The term "diagnosis" may also refer to a method or agent used to distinguish between two or more conditions associated with similar or identical symptoms.

The term "diagnosis" may also refer to a method or agent used to choose the most promising treatment regime for a patient. In other words, the method or agent may relate to selecting a treatment regimen for a subject. For example, detection of autoantibodies may indicate that immunosuppressive therapy is to be selected, which may include administrating one or more immunosuppressive drugs to the patient.

One object of the present invention relates to a complex comprising an antibody, preferably autoantibody, binding to a polypeptide. Such a complex may be used or detected as a part of a method for diagnosing a disease. A liquid sample comprising antibodies from a subject may be used to practice the method. Such a liquid sample may be any bodily fluid comprising a representative set of antibodies from the subject, preferably a sample comprising antibodies of the IgG immunoglobulin class from the subject. For example, a sample may be cerebrospinal fluid (CSF), blood or blood serum, lymph, insterstitial fluid and is preferably serum or CSF, more preferably serum.

The contacting of a liquid sample comprising antibodies with a polypeptide may be carried out by incubating an immobilized form of the provided polypeptide in the presence of a sample comprising antibodies under conditions that are compatible with the formation of a complex comprising the polypeptide and antibody, preferably an autoantibody, binding to the polypeptide. The liquid sample, then depleted of the antibodies binding to the polypeptide may be removed subsequently, followed by one or more washing steps. Finally, the complex comprising the antibody and polypeptide may be detected. In a preferred embodiment, the term "conditions compatible with the formation of the complex" are conditions that allow for the specific antigen-antibody interactions to build up a complex comprising the polypeptide and antibody. In one embodiment, such conditions may comprise incubating the polypeptide in a sample diluted 1:100 in PBS buffer for 30 minutes at 25° C. The term "autoantibody", as used herein, refers to an antibody binding specifically to an endogenous molecule of an animal, preferably mammal, which produces said autoantibody, wherein the level of the antibody is more preferably elevated compared to the average of any other antibodies binding specifically to the endogenous molecule. In one embodiment, the autoantibody is an autoantibody binding to flotillin1 and/or flotillin2.

In one embodiment, detection of a complex for the prognosis, diagnosis, methods or test kit according to the present invention comprises using a technique selected from the group consisting of immunodiffusion technique, immunoelectrophoretic technique, light scattering immunoassay, light scattering immunoassay, agglutination technique, labeled immunoassay selected from the group consisting of radiolabeled immunoassays, enzyme immunoassays, chemiluminscence immunoassays, and immunofluorescence techniques. These methods could be found, for example, in Zane, H. D. (2001), Immunology—Theoretical & Practical Concepts in Laboratory Medicine, W. B. Saunders Company, in particular in Chapter 14.

Alternatively, a sample comprising tissue comprising the polypeptide rather than a liquid sample may be used. The tissue sample is preferably from a tissue expressing endogenous flotillin1 and/or flotillin2. The sample, which may be in the form of a tissue section fixed on a carrier, for example, a glass slide for microscopic analysis, may then be contacted with the provided antibody, preferably an autoantibody, binding to the polypeptide. The antibody is preferably labeled to allow for distinction from the endogenous antibodies binding to the polypeptide, so that newly formed complexes may be detected and, optionally, quantified. If the amount of the formed complexes is lower than the amount found in the sample taken from a healthy subject, the subject from whom the examined sample has been taken is likely to suffer from the disease.

Any data demonstrating the presence or absence of a complex comprising the antibody and polypeptide may be correlated with reference data. For example, the detection of said complex indicates that the patient who provided the analyzed sample has suffered, is suffering or is likely to suffer in the future from the disease. If the patient has been previously diagnosed and the method for obtaining diagnostically relevant information has been run again, the amount of the detected complex in both runs may be correlated to find out about the progression of the disease and/or success of the treatment. For example, if the amount of the complex has increased, this suggests that the disorder is progressing, likely to manifest in the future and/or that any treatment attempted has been unsuccessful.

In one embodiment, a microplate, membrane ELISA, dot blot, or line blot could be used to carry out the diagnostic method. An example of the experimental setup could be found in, for example, Raoult, D., and Dasch, G. A. (1989), The line blot: an immunoassay for monoclonal and other antibodies. Its application to the serotyping of gram-negative bacteria, J. Immunol. Methods, 125 (1-2), 57-65; WO2013041540.

In another embodiment, prognosis, diagnosis, methods or a test kit contemplate use of indirect immunofluorescence. Techniques and preparations of suitable samples could be found in, for example, U.S. Pat. No. 4,647,543; Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007. Suitable reagents, devices, and software packages are commercially available, for example, from EUROIMMUN, Lübeck, Germany.

A sample subjected to a test determining only whether an autoantibody binding to flotillin1 and/or flotillin2 is present, but it is preferred that diagnostic methods, tests, devices and the like contemplate determining the presence of autoantibodies against a variety of antigens relating to neurological autoimmune diseases or variants thereof, preferably selected from the group consisting of Hu, Yo, Ri, CV2, PNMA1, PNMA2, DNER/Tr, ARHGAP26, ITPR1, ATP1A3, NBC1, Neurochrondrin, CARPVIII, Zic4, Sox1, Ma, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGI1, VGCC and mGluR1 and CASPR2, which antigens are preferably immobilized, for example on a medical device such as a line blot. The diagnostically relevant markers Neurochrondrin, (EP15001186), ITPR1 (EP14003703.7), NBC1 (EP14003958.7) and ATP1A3, also referred to as alpha 3 subunit of human neuronal Na(+)/K(+) ATPase (EP14171561.5), have been described.

According to one embodiment, an antibody, preferably an autoantibody binding to the provided polypeptide is used for the diagnosis of a disease, is provided. Examples of methods for purifying antibodies could be found in, for example, Hermanson, G. T., Mallia, A. K., and Smith, P. K. (1992), Immobilized Affinity Ligand Techniques, San Diego: Academic Press. Briefly, an antigen binding specifically to an antibody of interest, which antigen is a polypeptide, is immobilized and used to purify, via affinity chromatography, the antibody of interest from an adequate source. A liquid sample comprising antibodies from a patient suffering from a neurological disorder identified by the inventors may be used as a source.

According to one embodiment, an antibody, for example, an autoantibody, is provided that is capable of binding specifically to the provided polypeptide. The term "antibody", as used herein, refers to any immunoglobulin-based binding moieties, more preferably one comprising at least one immunoglobulin heavy chain and one immunoglobulin light chain, including, but not limited to, monoclonal and polyclonal antibodies as well as variants of an antibody, in particular fragments, which binding moieties are capable of binding to the respective antigen, more preferably specifically binding to it. The term "binding specifically", as used herein, means that the binding is stronger than a binding reaction characterized by a dissociation constant of $1\times10^{-5}$M, more preferably $1\times10^{-7}$M, more preferably $1\times10^{-8}$M, more preferably $1\times10^{-9}$M, more preferably $1\times10^{-10}$ M, more preferably $1\times10^{-11}$M, more preferably $1\times10^{-12}$M, as determined by surface plasmon resonance using Biacore equipment at 25° C. in PBS buffer at pH 7. The antibody may be a part of an autoantibody preparation which is heterogeneous or may be a homogenous autoantibody, wherein a heterogeneous preparation comprises a plurality of different autoantibody species as obtainable by the preparation from sera of human donors, for example, by affinity chromatography using an immobilized antigen to purify any autoantibody capable of binding to said antigen. The antibody may be glycosylated or non-glycosylated. Methods that may be used for the identification, production, and purification of antibodies and variants thereof are described, for examples, in EP 2 423 226 A2 and references therein. An antibody may be used as a diagnostic agent, by itself, or in combination, for example, in complex with a polypeptide.

Another object of the present invention is to provide a method for isolating an antibody, preferably an autoantibody, binding to a polypeptide, comprising a) contacting a sample comprising the antibody with the polypeptide such that a complex is formed, b) isolating the complex formed in a), c) dissociating the complex isolated in b), and d) separating the antibody from the polypeptide. A sample from a patient suffering from a novel neurological disorder identified by the inventors may be used as a source of the antibody. Suitable methods of purification are described in, for example, the Handbooks "Affinity chromatography," "Strategies for Protein Purification" and "Antibody Purification" (2009/2010), published by GE Healthcare Life Sciences, and in Philips, Terry, M., Analytical techniques in immunochemistry, 1992, Marcel Dekker, Inc.

Still another object of the present invention is a pharmaceutical composition comprising a polypeptide, which composition is preferably suitable for administration to a subject, preferably a mammalian subject, more preferably to a human. The pharmaceutical composition may comprise a pharmaceutically acceptable carrier. The pharmaceutical composition may, for example, be administered orally, parenterally, by inhalation spray, topically, by eye drops, rectally, nasally, buccally, vaginally or via an implanted reservoir, wherein the term "parentally", as used herein, comprises subcutaneous, intracutaneous, intravenous, intramuscular, intra-articular, intrasynovial, intrasternal, intrathecal, intralesional and intracranial injection or infusion techniques. The pharmaceutical composition may be provided in suitable dosage forms, for example, capsules, tablets and aqueous suspensions and solutions, preferably in a sterile form. It may be used in a method of treatment of a disease, comprising administration of an effective amount of the polypeptide to a subject in need thereof. In one embodiment, a vaccine comprises the provided polypeptide, optionally, comprising an auxiliary agent such as an adjuvant or a buffer, and the use of the polypeptide for the preparation of a vaccine.

A medical or diagnostic device, preferably coated with the autoantibody and/or polypeptide, is provided. Preferably, the medical or diagnostic device comprises the polypeptide in the form that allows contacting it with an aqueous solution, more preferably a liquid human sample, in a straightforward manner. In particular, the polypeptide may be immobilized on the surface of a carrier such as an artificial carrier, preferably selected from the group consisting of glass plates or slides, biochips, microtiter plates, beads, for example magnetic beads, apharesis devices, chromatography columns, membranes or the like. Exemplary medical devices include line blots, microplates, glass slides for microscopy, beads and biochips. In addition to the provided polypeptide, the medical or diagnostic device may comprise additional polypeptides, preferably in an enriched, isolated and/or recombinant form, for example, positive or negative controls or other antigens binding to autoantibodies of diagnostic value, particularly those related to other diseases associated with one or more identical or similar symptoms. The medical device, preferably comprising one diagnostically useful carrier comprising one or more antigens, preferably more than one antigen, or more than one diagnostically useful carrier each comprising one or more antigens, preferably one antigen, may comprise, in addition to the polypeptide, one or more antigens from the group consisting of Hu, Yo, Ri, CV2, PNMA1, PNMA2, DNER/Tr, ARHGAP26, ITPR1, ATP1A3, NBC1, Neurochrondrin, CARPVIII, Zic4, Sox1, Ma, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGI1, VGCC and mGluR1 and CASPR2, preferably a combination comprising at least the provided polypeptide, aquaporin-4 and MOG. Variants of each antigen having, as a biological activity, the ability to bind to the respective autoantibody to the antigen, may be used instead of the antigen.

A kit, preferably for diagnosing a disease, is also provided. The kit may comprise instructions detailing how to use the kit and a means for contacting a polypeptide with a bodily fluid sample from a subject, preferably a human subject, for example, a line blot, wherein the provided polypeptide is immobilized on the line blot. Furthermore, the kit may comprise a positive control, for example, a batch of an autoantibody or recombinant antibody known to bind to the polypeptide and a negative control, for example, a protein having no detectable affinity to the polypeptide such as bovine serum albumin. Finally, the kit may comprise a standard solution of an antibody or antigen for preparing a calibration curve.

In one embodiment, the kit comprises a means for detecting an antibody, more preferably an autoantibody, binding to a polypeptide, preferably by detecting a complex comprising the polypeptide and antibody binding to the polypeptide. The means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class of antibodies. A multitude of methods and means for detecting such a complex could be found in, for example, Philips, Terry, M., Analytical techniques in immunochemistry, 1992, Marcel Dekker, Inc.

A polypeptide comprising flotillin1 and/or flotillin2 may be produced or provided in the form of a cell comprising and/or expressing a nucleic acid encoding the polypeptide.

If a nucleic acid comprising a sequence that encodes the polypeptide or a variant thereof is used, the nucleic acid may be an unmodified nucleic acid. In one embodiment, the nucleic acid is a nucleic acid that does not occur in nature and comprises, compared to the natural nucleic acid, at least one modification, for example, an isotopic content or chemical modifications, for example, a methylation, sequence modification, label or the like indicative of synthetic origin. In one embodiment, the nucleic acid is a recombinant nucleic acid or a part of a nucleic acid, and is, in a more preferred embodiment, a part of a vector, in which it may be functionally linked with a promoter that allows for expression, preferably overexpression, of the nucleic acid. A variety of suitable vectors including commercially available, for example from Origene, could be used. For example, a vector encoding fusion constructs with a C-terminal GFP may be used. The cell may be a eukaryotic or prokaryotic cell, preferably an eukaryotic cell, such as an yeast cell, and is more preferably a mammalian, more preferably a human cell such as a HEK293 cell. Examples of a mammalian cell include, but not limited to, a HEK293, CHO, and COS-7 cell. The cell comprising the nucleic acid encoding for a polypeptide may be a recombinant cell or an isolated cell wherein the term "isolated" means that the cell is enriched such that, compared to the environment of the wild type of said cell, fewer cells of other differentiation or species or in fact no such other cells are present.

Objects of the present invention are not only related to diagnosis, but also to prevention or treatment of a disease, more specifically a method for preventing or treating a disease comprises a) reducing a concentration of autoantibodies binding to a polypeptide in subject's blood and/or b) administering one or more immunosuppressive pharmaceutical substances, preferably selected from the group consisting of rituximab, prednisone, methylprednisolone, cyclophosphamide, mycophenolatemofetil, intravenous immunoglobulin, tacrolimus, cyclosporine, methotrexate, azathioprine and/or a pharmaceutical composition.

A number of sequences are disclosed in this application, more specifically SEQ ID NO 1, which represents the nucleotide sequence of the expression vector pTriEX-1-Flotillin-1[human]-His, SEQ ID NO 2, which represents the polypeptide sequence of human flotillin1 attached to a C-terminal His tag, SEQ ID NO 3, which represents the nucleotide sequence of expression vector pTriEX-1-Flotillin-1[human], SEQ ID NO 4, which represents the polypeptide sequence of human flotillin1, SEQ ID NO 5, which represents the nucleotide sequence of expression vector pTriEX-1-Flotillin-2[human]-His, SEQ ID NO 6, which represents the polypeptide sequence of human flotillin2 attached to a C-terminal His tag, SEQ ID NO 7, which represents the nucleotide sequence of expression vector pTriEX-1-Flotillin-2[human], and SEQ ID NO 8, which represents the polypeptide sequence of human flotillin2.

Having generally described this invention, a further understanding can be obtained by reference to certain specific examples which are provided herein for purposes of illustration only, and are not intended to be limiting unless otherwise specified.

Examples

Summary

The following examples demonstrate that a patient suffering from optic neuritis, more specifically vision impairment, headache and brain lesions, was clinically assessed, but the molecular basis of their disease remained unknown. Their blood was screened, but contained no autoantibodies to known neurological markers. An autoantibody was isolated based on the characteristic staining pattern following the reaction with several mammalian tissues, more specifically cerebellum and hippocampus from rat and pig.

Immunoprecipitation, mass spectrometry and competitive binding studies using recombinant flotillin1 and flotillin2 revealed flotillin1 and flotillin2 as the targets of said antibody. 34 sera from patients with various neural autoantibodies (anti-NMDAR, anti-Hu, anti-Yo, anti-Ri, anti-AQP4, anti-LGI1, anti-CASPR2) and from 226 healthy controls showed no reaction when contacted with recombinant flotillin 1/2, confirming that the provided method is a specific assay.

The patient responded positively to immunosuppressive treatment to the effect. Visual symptoms completely vanished.

Characterization of Patient

Healthy female patient (34 years old) initially presented with blurred vision, local retrobulbar pain, and with reduced intensity of red color vision of the right eye which started five days before presentation. Except for there was an unremarkable medical history without hints for any autoimmune disease in the near family except for suspicion of multiple sclerosis in a grandmother on the mother's side. The clinical-neurological examination had revealed an impaired vision of right eye (0.6; left: 1.0). The testing of visual evoked potentials revealed a severe disturbation of processing of optical afferences. Moreover, further electrophysiological testing also revealed a slight disturbance of sensitive afferences from the left leg, but normal responses after the transcranial magnetic stimulation to all four extremities. Cranial MRI revealed signs of inflammation (contrast enhancement) of the right optical nerve as well as several small subcortical white matter lesions (without signs of blood brain barrier damage), typical for a demyelinating disease such as multiple sclerosis (FIG. 1). In FIG. 1, the female patient was presented with optic neuritis of suspected autoimmune origin. Lesions remained stable under immunomodulatory therapy over 5 month with interferone beta. T2 weighted magnetic resonance imaging (A, C), and flair imaging (B, D) of the same female 34 year old patient at initial presentation (A, B), and after 6 month (C, D) are shown. Blood testing showed normal values for renal and hepatic function, normal electrolytes, and a normal number and distribution of red and white cells. Testing for autoantibodies in the serum revealed no significant findings: rheumatoid factor, pANCA, AMA, anti-phospholid, anti-*Borrelia* (IgG/IgM) and anti-*Treponema* were negative; ANA were present at a titer of 1:320. CSF revealed a mild pleocytosis (9 cells/µL), normal protein (269 mg/L), local IgG synthesis (53%), and oligoclonal bands that were absent in serum. Anti-AQP4 was neither detectable in CSF nor in serum.

The patient was treated with intravenous glucocorticoid pulse therapy under suspicion of autoimmune neuritis of the optical nerve. A clinically isolated syndrome was assumed and an immunomodulation with betaferone was initiated. 5 months later, the visual symptoms had disappeared completely.

22 month after the onset of the initial symptoms, the patient was presented with a stable clinical situation without further progress of the neurological symptoms. A control lumbar puncture revealed an autochthonous antibody production with oligoclonal bands in the CSF and a mild pleocytosis of 5 cells/µL CSF.

Indirect Immunofluorescence Assay (IFA)

Slides with a biochip mosaic including brain tissue cryosections (hippocampus of rat, cerebellum of rat, monkey, and pig) and HEK293 cells individually expressing 30 recombinant brain antigens was used for IFA. The slides were incubated with 70 µL of sample diluted in PBS, 0.2% Tween-20 (IFA buffer) at room temperature for 30 min, flushed with IFA buffer and immersed in IFA buffer for 5 min. Subsequently, polyclonal goat anti-human pan-IgG (EUROIMMUN) or monoclonal murine anti-human IgG1, IgG2, IgG3, or IgG4 (Sigma-Aldrich), each labelled with fluorescein isothiocyanate (FITC), were incubated at room temperature for 30 min. Slides were then washed again, embedded in PBS-buffered, DABCO containing glycerol (approximately 20 µL per mosaic) and examined by two independent observers using a laser scanning microscope (LSM700, Zeiss, Jena, Germany). Positive and negative controls were included. Samples were categorized based on tissue patterns and fluorescence intensity of transfected cells in the direct comparison with non-transfected cells and control samples. Endpoint titers refer to the highest dilution showing visible fluorescence. Live-cell IFA with primary hippocampal neurons was conducted (Dalmau J, Gleichman A J, Hughes E G, Rossi J E, Peng X, Lai M, et al. Anti-NMDA-receptor encephalitis: case series and analysis of the effects of antibodies. Lancet Neurol 2008 Oct. 11).

A polyclonal rabbit antibody against flotillin2 (Sigma-Aldrich, dilution 1:100) was used in some experiments in the first step followed by incubation with anti-rabbit IgG-Cy3 (Jackson Research, Suffolk, United Kingdom). Cell nuclei were visualized by DNA staining with TO-PRO3 Iodide (dilution 1:2000) (ThermoFisher Scientific, Schwerte, Germany). Recombinant antigens were mixed with a diluted serum sample 1 h prior to WA (see Stöcker W, Otte M, Ulrich S, Normann D, Finkbeiner H, Stöcker K, et al. Autoimmunity to pancreatic juice in Crohn's disease. Results of an autoantibody screening in patients with chronic inflammatory bowel disease. Scand J Gastroenterol Suppl 1987; 139:41-52) for neutralization experiments.

In FIG. 2, cryosections were incubated with patient serum (1:100) or CSF (undiluted) in the first step, and with FITC labelled goat anti-human IgG in the second step. Nuclei were counterstained by incubation with TO-PRO-3 iodide (blue). A fine-granular staining of the molecular layers (ML) and a patchy staining of the granular layer was obtained. On Hippocampus the outer ML was more intense than the inner ML.

Histo-Immunoprecipitation and Identification of the Antigen

Cerebellum from rat or pig was dissected and shock-frozen in −160° C. isopentane. The tissue was then cryosected (4 µm) with a SM2000R microtome (Leica Microsystems, Nussloch, Germany), placed on glass slides, dried and stored at −196° C. For HIP, slides were incubated with patient's serum (diluted 1:100) at 4° C. for 3 hours followed by 3 washing steps with IFA buffer. The tissue was then extracted with a solubilization buffer (100 mmol/L tris-HCl pH 7.4, 150 mmol/L sodium chloride, 2.5 mmol/L EDTA, 0.5% (w/v) deoxycholate, 1% (w/v) Triton X-100 containing protease inhibitors) at room temperature for 30 minutes. The resulting suspension was homogenized and centrifuged at 16,000×g at 4° C. for 15 minutes. Immunocomplexes were precipitated from the clear supernatant with Protein G Dynabeads (ThermoFisher Scientific, Dreieich, Germany) at 4° C. overnight, washed 3 times with PBS, and eluted with PBS, 5 mmol/L dithiothreitol, 1% (w/v) sodium dodecylsulfate at 95° C. for 10 minutes. The eluates were analysed by SDS-PAGE and mass spectrometry or Western blot.

In FIG. 3, cyosections of rat or pig cerebellum were incubated with the patient's serum (1:200), washed in PBS and solubilized using detergents. The solution was incubated with protein-G-coated magnetic beads. The immunocomplexes were eluted by SDS and subjected to SDS-PAGE analysis and Western blot.

Recombinant Expression of Flotillin1 and Flotillin2 in HEK293

The cloning of expression vectors (SEQ ID NOs: 1 and 3 encoding a polypeptide comprising flotillin1; SEQ ID NOs: 5 and 7 encoding a polypeptide comprising flotillin2) was performed using standard methods. In order to prepare substrates for IFA, HEK293 were seeded on sterile cover glasses, transfected, and allowed to express flotillin1 and flotillin2 either individually or in conjunction for 48 hours. Cover glasses were washed with PBS, fixed with either acetone for 10 minutes at room temperature, air-dried, cut into millimeter-sized biochips and used as substrates in IFA as described. Alternatively, cells were transfected in standard T-flasks and the cells were harvested after 5 days. The cell sediment was extracted with solubilization buffer. The extracts were stored in aliquots at −80° C. until further use.

Studies with a Larger Cohort of Patients

Sera from 49 patients with various neural autoantibodies, including 20 with autoantibodies against AQP4 (titers up to 1:3,200), and from 226 healthy controls were analyzed by IFA. None of the sera reacted with HEK293-flotillin-1, HEK293-flotillin-2, and HEK293-flotillin-1/2.

The anti-flotillin-1/2 status was then determined retrospectively in 224 samples for which a general broad neural autoantibody screening, including the aforementioned parameters, had been conducted in the Clinical Immunological Laboratory Lubeck, and for which a neural tissue-reactive IgG autoantibody without known antigen-specificity had been reported. Serum anti-flotillin-1/2 was revealed in four patients (P2-P5 in Table 1, titers: 1:1,000, 1:1,000, 1:10,000, 1:10,000). Patients P2, P3, and P5 also showed anti-flotillin-1/2 in CSF (titers: 1:3.2, 1:100, 1:1,000). For P4, CSF was not available. Specific antibody indices >4 were calculated for P1, P3, and P5. Additional follow-up sera of the patients were analyzed when available and showed that the anti-flotillin-1/2 titers of P1, P2, and P4 were stable over a period of 18, 24, and 72 months, respectively. Serum of P5 showed a reduction to 1:320 seven weeks after plasma exchange.

HEK293-flotillin-1/2 was then integrated in the broad autoantibody screening regimen of the reference laboratory. In a cohort of 521 consecutive patients for whom a determination of anti-AQP4 was requested, eighteen were positive for anti-AQP4 while three exhibited anti-flotillin-1/2. For one of the latter medical records were accessible (serum: 1:1,000, no CSF, P6 in Table 1). An additional patient was identified during the diagnostic work-up of 150 consecutive unselected neurological patients (serum: 1:10, CSF negative, P7 in Table 1), and a further patient by screening of 57 anonymized, anti-AQP4- and anti-MOG-negative sera from patients with isolated ON (1:10, CSF not available).

In summary, all seven patients for whom medical records could be evaluated had radiological signs of disseminated demyelination, mild pleocytosis and OCB in CSF consistent with MS or a CIS suggestive of MS. Six of them showed optic neuritis. In all cases, the autoantibodies were of the subclass IgG1 and bound to flotillin-1/2 but not to individual flotillin-1 or flotillin-2. None of the patients displayed anti-AQP4 or anti-MOG antibodies.

European patent application No. EP 15001671.5 filed Jun. 4, 2015 and European patent application No. EP 1600200.2 filed Jan. 28, 2016, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method for detecting the presence of an autoantibody in a subject, comprising:
   obtaining a sample from a subject;
   exposing a complex comprising 1) flotillin1 or a variant thereof and 2) flotillin2 or a variant thereof, which is immobilized on a solid carrier, to the sample from the subject; and
   detecting whether the autoantibody is present in the sample by detecting the binding between the autoantibody and the complex.

2. The method according to claim 1, wherein said variant comprises at least 6 successive amino acids of the original sequence.

3. The method according to claim 1, wherein said variant comprises an amino acid sequence that is at least 40% identical with the reference amino acid sequence.

* * * * *